United States Patent
Kim et al.

(10) Patent No.: US 11,407,744 B2
(45) Date of Patent: Aug. 9, 2022

(54) COMPOUND AND PHARMACEUTICAL COMPOSITION COMPRISING SAME

(71) Applicant: AUTOPHAGYSCIENCES INC., Seoul (KR)

(72) Inventors: Jung Ju Kim, Seoul (KR); Seong-Won Song, Gunpo-si (KR); Hye Jeong Shin, Yongin-si (KR); Hyeongwan Choi, Seoul (KR)

(73) Assignee: AUTOPHAGYSCIENCES INC., Seoul (KR)

( * ) Notice: Subject to any disclaimer, the term of this patent is extended or adjusted under 35 U.S.C. 154(b) by 0 days.

(21) Appl. No.: 16/970,418

(22) PCT Filed: May 31, 2019

(86) PCT No.: PCT/KR2019/006606
§ 371 (c)(1),
(2) Date: Aug. 17, 2020

(87) PCT Pub. No.: WO2019/231290
PCT Pub. Date: Dec. 5, 2019

(65) Prior Publication Data
US 2021/0078987 A1    Mar. 18, 2021

(30) Foreign Application Priority Data

Jun. 1, 2018 (KR) ........................ 10-2018-0063496

(51) Int. Cl.
| | | |
|---|---|---|
| *C07D 409/14* | (2006.01) | |
| *C07D 307/68* | (2006.01) | |
| *C07D 333/38* | (2006.01) | |
| *C07D 405/04* | (2006.01) | |
| *C07D 405/12* | (2006.01) | |
| *C07D 405/14* | (2006.01) | |
| *C07D 409/04* | (2006.01) | |
| *C07D 409/12* | (2006.01) | |
| *A61P 1/16* | (2006.01) | |

(52) U.S. Cl.
CPC .............. *C07D 409/14* (2013.01); *A61P 1/16* (2018.01); *C07D 307/68* (2013.01); *C07D 333/38* (2013.01); *C07D 405/04* (2013.01); *C07D 405/12* (2013.01); *C07D 405/14* (2013.01); *C07D 409/04* (2013.01); *C07D 409/12* (2013.01)

(58) Field of Classification Search
CPC .. C07D 409/04; C07D 409/12; C07D 409/14; C07D 307/68; C07D 333/38; C07D 405/04; C07D 405/12; C07D 405/14
See application file for complete search history.

(56) References Cited

U.S. PATENT DOCUMENTS

| | | | |
|---|---|---|---|
| 8,729,273 B2 | 5/2014 | Song et al. | |
| 2008/0293716 A1* | 11/2008 | Drewry ................... | A61P 25/28 514/235.5 |
| 2018/0244644 A1 | 8/2018 | Kim et al. | |

FOREIGN PATENT DOCUMENTS

| | | |
|---|---|---|
| KR | 10-2016-0014975 A | 2/2016 |
| KR | 10-2017-0022790 A | 3/2017 |
| WO | WO 2004/110357 A2 | 12/2004 |
| WO | WO 2011-043568 A2 | 4/2011 |
| WO | WO 2012/085170 A2 | 7/2012 |
| WO | WO 2017-034242 A2 | 3/2017 |

OTHER PUBLICATIONS

Registry No. 890824-27-8, File REGISTRY on STN, Jul. 6, 2006.*
Haag, B. A. et al., "Practical one-pot preparation of magnesium di(hetero)aryl- and Magnesium dialkenylboronates for Suzuki-Miyaura cross-coupling reactions", Angewandte Chemie International Edition, 2011, vol. 50, p. 7290-7294.
Michaelides, M. R. et al., "Substituted hexahydrobenzo[f]thieno[c] quinolines as dopamine D1-selective agonists: synthesis and biological evaluation in vitro and in vivo", Journal of Medicinal Chemistry, 1997, vol. 40, p. 1585-1599.
International Search Report of PCT Application No. PCT/KR2019/006606, dated Sep. 5, 2019.
Daniel J. Klionsky, et al., "Autophagy as a regulated pathway of cellular degradation." Science (New York, N.Y.) vol. 290, No. 5497 (2000): pp. 1717-1721.
Beth Levine, et al., "Development by Self-Digestion: Molecular Mechanisms and Biological Functions of Autophagy", Developmental Cell, vol. 6, Issue 4, 2004, pp. 463-477, ISSN 1534-5807.
David C Rubinsztein, et al., "Autophagy modulation as a potential therapeutic target for diverse diseases", Nat Rev Drug Discov. 2012; vol. 11, No. 9, pp. 709-730.
Patrice Codogno, et al., "Autophagy in the liver", Journal of Hepatology, vol. 59, No. 2, pp. 389-391, 2013.
Pierre-Emmanuel Rautou, et al., "Autophagy in liver diseases", J Hepatol. , 2010, vol. 53, No. 6, pp. 1123-1134.
Mark J Czaja, et al. "Functions of autophagy in normal and diseased liver." Autophagy, vol. 9, No. 8 (2013), pp. 1131-1158.
Sunandini Sridhar, et al. "Autophagy and disease: always two sides to a problem." The Journal of Pathology, vol. 226, No. 2 (2012), pp. 255-273.
Augustine M K Choi, et al. "Autophagy in human health and disease," The New England Journal of Medicine, vol. 368, No. 7 (2013), pp. 651-662.
Jiang, Peidu, et al., "Autophagy and human diseases." Cell Research, vol. 24, No. 1 (2014), pp. 69-79.
Ju-Hyun Lee, et al., "Lysosomal proteolysis and autophagy require presenilin 1 and are disrupted by Alzheimer-related PS1 mutations", Cell, vol. 141, No. 7 (2010), pp. 1146-1158.

(Continued)

*Primary Examiner* — Rebecca L Anderson
(74) *Attorney, Agent, or Firm* — Pearl Cohen Zedek Latzer Baratz LLP

(57) ABSTRACT

The present disclosure relates to a novel compound and a pharmaceutical composition comprising the same. The compound according to the present disclosure has effects for activating autophagy, and thus can be valuably used for preventing or treating diseases associated with autophagy regulation.

2 Claims, 1 Drawing Sheet

(56) References Cited

OTHER PUBLICATIONS

Ai Ling Wang, et al., "Autophagy and Exosomes in the Aged Retinal Pigment Epithelium: Possible Relevance to Drusen Formation and Age-Related Macular Degeneration", PLoS ONE (2009), vol. 4, No. 1, p. e4160.
Yoshinobu Ichimura et al., "Pathophysiological Role of Autophagy: Lesson from Autophagy-Deficient Mouse Models", Experimental Animals, 2011, vol. 60, Issue 4, pp. 329-345.
Geoffrey C. Farrell, et al., "Nonalcoholic fatty liver disease: from steatosis to cirrhosis", *Hepatology*, 2006, vol. 43, 2 Suppl 1, pp. S99-S112.
Brent A. Neuschwander-Tetri, et al., "Nonalcoholic steatohepatitis: summary of an AASLD Single Topic Conference", *Hepatology*, 2003, vol. 37, No. 5, pp. 1202-1219 [published correction appears in Hepatology, Aug. 2003, vol. 38, No. 2, p. 536].
CP Day, "Steatohepatitis: a tale of two "hits"?", *Gastroenterology*. 1998, vol. 114, No. 4, pp. 842-845.
Rajat Singh, et al., "Autophagy regulates lipid metabolism", *Nature*, 2009, vol. 458, No. 7242, pp. 1131-1135.
Chemical Abstract compound, STN express. RN 1024394-17-9 Registry (Entered STN: Jun. 1, 2008).
Chemical Abstract compound, STN express. RN 1024265-75-5 Registry (Entered STN: Jun. 1, 2008).
Chemical Abstract compound, STN express. RN 866849-54-9 Registry (Entered STN: Nov. 7, 2005).
Office Action for Korean Patent Application No. 10-2019-0064328, dated Jul. 15, 2021.
Database Pubchem [Online] May 29, 2009, Ncbi: "5-(4-fluorophenyl)-N-propan-2-ylthiophene-2-carboxamide", XP055871529, Database accession No. 35807263.
Database Pubchem [Online] Dec. 12, 2007, Ncbi: "N-isopropyl-5-phenylthiophene-2-carboxamide | C14H15NOS—PubChem", XP055871538, Database accession No. 23602124.
Database Chemical Abstracts [Online] Jan. 1, 1998, Wang et al: Synthesis and biological activity of N-aryl-5-aryl-2-furoamides and N-(5-aryl)-2 furoyl-N'-aryloxyacetylhydrazines, Gaodeng Xuexiao Huaxue Xuebao (1998),19(8),1274-1276, XP055871551,Database accession No. 1998:590044.
Database Pubchem [Online] May 29, 2009, Ncbi: "Sdccgsbi-0121524. P001", XP055871560, Database accession No. 39834670.
Bensaid Souhila et al.: "Solvent-Free Palladium-Catalyzed Direct Arylation of Heteroaromatics with Aryl Bromides", CHEMSUSCHEM, vol. 5, No. 8, Jul. 25, 2012, pp. 1559-1567.
Arkady S. Pilipenko et al.: "Furan ring opening-indole ring closure: recyclization of 2-(2-aminophenyl)furans into 2-(2-oxoalkyl)indoles", Tetrahedron, vol. 68, No. 2, Oct. 31, 2011, pp. 619-627.
Database Pubchem [Online] Nov. 27, 2010, Ncbi: "Ethyl 5-(4-isoquinolyl)-2-furoate", XP055871605, Database accession No. 49761862.
Chen Yi-Hung et al.: "Preparation of Aryl and Heteroaryl Indium (III) Reagents by the Direct Insertion of Indium in the Presence of LiCI", Angewandte Chemie International Edition, vol. 47, No. 40, Sep. 22, 2008, pp. 7648-7651.
Database Pubchem [Online] Nov. 27, 2010, Ncbi: "Ethyl 5-(3-quinolyl)-2-furoate", XP055871617, Database accession No. 49761863.
Carsten D. Siebert: "Das Bioisosterie-Konzept: Arzneistoffentwicklung", Chemie In Unserer Zeit, vol. 38, No. 5, 2004, pp. 320-324.
Search Report for European Patent Application No. 1981141.5, dated Dec. 20, 2021.
N. Juwaini, et al., "Catalytic Regioselective Oxidative Coupling of Furan-2-Carbonyls with Simple Arenes" ACS Catalysis, 2012, vol. 2, No. 8, pp. 1787-1791.
H. Yue, et al., "Selective Reductive Removal of Ester and Amide Groups from Arenes and Heteroarenes through Nickel-Catalyzed C—O and C—N Bond Activation", *Angewadte Chemie International Edition* 2017, vol. 56, pp. 3972-3976.
Y. Zhu, et al., "Triflic Acid-Catalyzed Cycloisomerization Reactions of Donor-Acceptor Cyclopropanes: Access to Alkyl 5-Arylfuran-2-carboxylates", J Org Chem., Jun. 3, 2016, vol. 81, No. 11, pp. 4829-4834.
G. Gowda et al., "Base catalyzed reaction of ethyl thioglycolate with ß-aryl-ß(methylthio) acroleins: a general method for the synthesis of 2-carbethoxy-5-substituted/4,5-annulated thiophenes in high overall yields", Tetrahedron Letters, vol. 57, Issue 8, 2016, pp. 928-931, ISSN 0040-4039.
Chemical Abstract compound, STN express. RN 1996626-80-2 (Entered STN: Sep. 20, 2016.).
Chemical Abstract compound, STN express. RN 1996626-81-3 (Entered STN Sep. 20, 2016.).
Chemical Abstract compound, STN express. RN 1997317-97-1 (Entered STN Sep. 21, 2016.).
Chemical Abstract compound, STN express. RN 199458-92-9 (Entered STN Jan. 8, 1998.).
Chemical Abstract compound, STN express. RN 199458-93-0 (Entered STN Jan. 8, 1998.).
Chemical Abstract compound, STN express. RN 213911-05-8 (Entered STN Nov. 8, 1998.).
Chemical Abstract compound, STN express. RN 213911-06-9 (Entered STN Nov. 8, 1998.).
Chemical Abstract compound, STN express. RN 69202-27-3 (Entered STN Nov. 16, 1984.).
Chemical Abstract compound, STN express. RN 199458-84-9 (Entered STN Jan. 8, 1998.).
Chemical Abstract compound, STN express. RN 338793-89-8 (Entered STN May 29, 2001.).
Chemical Abstract compound, STN express. RN 199457-61-9 (Entered STN Jan. 8, 1998.).
Chemical Abstract compound, STN express. RN 199457-69-7 (Entered STN Jan. 8, 1998.).
Chemical Abstract compound, STN express. RN 199457-70-0 (Entered STN Jan. 8, 1998.).
Chemical Abstract compound, STN express. RN 14597-62-7 (Entered STN Nov. 16, 1984.).
Chemical Abstract compound, STN express. RN 834884-73-0 (Entered STN Feb. 21, 2005.).
Chemical Abstract compound, STN express. RN 2143552-69-4 (Entered STN Nov. 16, 2017.).
Chemical Abstract compound, STN express. RN 2109732-66-1 (Entered STN Aug. 7, 2017.).
Chemical Abstract compound, STN express. RN 1127217-38-2 (Entered STN Mar. 26, 2009.).
Chemical Abstract compound, STN express. RN 1883530-67-3 (Entered STN Mar. 15, 2016.).
Chemical Abstract compound, STN express. RN 2061375-71-9 (Entered STN Jan. 29, 2017.).
Chemical Abstract compound, STN express. RN 1087349-10-7 (Entered STN Dec. 21, 2008.).
Chemical Abstract compound, STN express. RN 1259059-81-8 (Entered STN Jan. 12, 2011.).
Chemical Abstract compound, STN express. RN 11187163-71-8 (Entered STN Oct. 2, 2009.).
Chemical Abstract compound, STN express. RN 1820884-42-1 (Entered STN Nov. 18, 2015.).
Chemical Abstract compound, STN express. RN 1809269-92-8 (Entered STN Oct. 5, 2015.).
Chemical Abstract compound, STN express. RN 1127219-38-2 (Entered STN Mar. 26, 2009.).
Chemical Abstract compound, STN express. RN 52939-06-7 (Entered STN Nov. 16, 1984.).
Chemical Abstract compound, STN express. RN 1807820-88-7 (Entered STN Sep. 21, 2015.).
Chemical Abstract compound, STN express. RN 1639853-78-3 (Entered STN Dec. 30, 2014.).
Chemical Abstract compound, STN express. RN 1361151-66-7 (Entered STN Mar. 16, 2012.).
Chemical Abstract compound, STN express. RN 834884-75-2 (Entered STN Feb. 21, 2005.).
Chemical Abstract compound, STN express. RN 1486471-03-7 (Entered STN Dec. 3, 2013.).

(56) References Cited

OTHER PUBLICATIONS

Chemical Abstract compound, STN express. RN 1639853-69-2 (Entered STN Dec. 30, 2014.).
Chemical Abstract compound, STN express. RN 50971-49-8 (Entered STN Nov. 16, 1984.).
Chemical Abstract compound, STN express. RN 1024449-36-2 (Entered STN Jun. 1, 2008.).
Chemical Abstract compound, STN express. RN 229467-29-2 (Entered STN Jul. 30, 1999.).
Chemical Abstract compound, STN express. RN 80387-66-2 (Entered STN Nov. 16, 1984.).
Chemical Abstract compound, STN express. RN 299203-59-1 (Entered STN Oct. 25, 2000.).
Chemical Abstract compound, STN express. RN 1414997-92-4 (Entered STN Dec. 17, 2012.).
Chemical Abstract compound, STN express. RN 1433878-83-1 (Entered STN May 31, 2013.).
Chemical Abstract compound, STN express. RN 148682-16-0 (Entered STN Jul. 14, 1993.).
Chemical Abstract compound, STN express. RN 1186369-13-0 (Entered STN Sep. 27, 2009.).
Chemical Abstract compound, STN express. RN 1035235-06-3 (Entered STN Jul. 22, 2008.).
Chemical Abstract compound, STN express. RN 1050421-30-1 (Entered STN Sep. 18, 2008.).
Chemical Abstract compound, STN express. RN 1309446-48-7 (Entered STN Jun. 15, 2011.).
Chemical Abstract compound, STN express. RN 138628-95-2 (Entered STN Jun. 18, 2012.).
Chemical Abstract compound, STN express. RN 1330033-66-3 (Entered STN Sep. 8, 2011.).
Chemical Abstract compound, STN express. RN 1354929-08-0 (Entered STN Feb. 1, 2012.).
Chemical Abstract compound, STN express. RN 1353658-83-9 (Entered STN Jan. 19, 2012.).
Chemical Abstract compound, STN express. RN 55578-81-9 (Entered STN Nov. 16, 1984.).
Chemical Abstract compound, STN express. RN 62642-13-1 (Entered STN Nov. 16, 1984.).
Chemical Abstract compound, STN express. RN 329196-23-8 (Entered STN Mar. 28, 2001.).
Chemical Abstract compound, STN express. RN 1269086-33-0 (Entered STN Mar. 21, 2011.).
Chemical Abstract compound, STN express. RN 313394-67-1 (Entered STN Jan. 10, 2001.).
Chemical Abstract compound, STN express. RN 337931-71-2 (Entered STN May. 24, 2001.).
Chemical Abstract compound, STN express. RN 1802325-30-9 (Entered STN Aug. 20, 2015.).
Chemical Abstract compound, STN express. RN 958746-60-6 (Entered STN Dec. 19, 2007.).
Chemical Abstract compound, STN express. RN 1802325-34-3 (Entered STN Aug. 20, 2015.).
Chemical Abstract compound, STN express. RN 864454-63-7 (Entered STN Oct. 4, 2005.).
Listing of chemical structures of CAS (Chemical Abstracts System) compounds listed in references 6-65 above.
Office Action for Korean Patent Application No. 10-2019-0064328, dated Feb. 26, 2021.
Office Action for Indian Patent Application No. 202047049110, dated May 31, 2022.
Office Action for Japanese Patent Application No. 2020-550741 dated Jun. 10, 2022.
Registry (STN) [online], May 16, 2019, 2308760-81-6.
Masakatsu Nozaki et al., Medicinal Chemistry, 1995, p. 98-99.

* cited by examiner

COMPOUND AND PHARMACEUTICAL COMPOSITION COMPRISING SAME

CROSS-REFERENCE TO RELATED APPLICATIONS

This application is a National Phase Application of PCT International Application No. PCT/KR2019/006606, International Filing Date May 31, 2019, claiming priority of Korean Patent Application No. 10-2018-0063496, filed Jun. 1, 2018.

FIELD OF THE INVENTION

The present disclosure relates to a novel compound and a pharmaceutical composition comprising the same. The compound according to the present disclosure has effects for activating autophagy and thus, can be valuably used for preventing or treating various diseases, particularly liver diseases.

BACKGROUND ART

Autophagy is a process by which eukaryotic cells digest their own cellular organs and old lived proteins as a kind of metabolic process. The process is closely associated with cellular growth, differentiation and homeostasis, and is a proteolytic process that is essential for maintaining cellular homeostasis and genetic stability by degrading aged or dysfunctional organelles and damaged proteins not possessing their native three dimensional structures. Further, the process is the only way to digest "long lived" or "broken" cell organs as above, and it appears in all eukaryotic cells, from yeast to mammals. ((1) Science, 290, 1717-1721, 2000, (2) Developmental cell, 6, 463-477, 2004).

In most in-vivo tissues, autophagy occurs at an appropriate level for the continuous metabolic turnover of intracellular components, and under certain conditions, autophagy is activated, making the energy necessary for cell survival and recycling nutrients. Therefore, the regulation of autophagy is a very important process in vivo. In addition, the fact that autophagy can be activated by certain drugs suggests that the process of autophagy can be a potential therapeutic target for diverse diseases (Nat Rev Drug Discov, 11(9), 709-730, 2012).

When dysregulation of autophagy occurs, it leads to the accumulation of proteins to be removed, which causes various diseases. As these diseases, typically, liver disease ((1) J Hepatol, 59, 389-391, 2013), (2) J Hepatol, 53, 1123-1134, 2010, (3) Autophagy, 9, 1131-1158, 2013), metabolic diseases such as obesity, diabetes, arteriosclerosis ((1) J Pathol, 226, 255-273, 2012, (2) N Engl J Med, 368, 651-662, 2013, (3) Cell Res, 24, 69-79, 2014), age-related macular degeneration (PLOS One, 4, e4160, 2009), degenerative brain disease (Cell, 7, 1146-1158, 2010.), pulmonary fibrosis, heart disease, inflammatory bowel disease, etc. are known. Further, it has been reported that the deficiency of autophagy-related genes (Atg) of systemic or specific tissues of various organisms including mice causes serious disorders (Exp Anim, 60, 329-345, 2011). This also demonstrates the importance of autophagy regulatory function.

As such, since autophagy is associated with various diseases, the development of substances capable of regulating the activity of autophagy is a clinically important issue.

Among various diseases related to autophagy, the liver, which is also a representative model of autophagy research, is characterized by: 1) very excellent reproductivity, 2) an important metabolic organ, and 3) an organ that is exposed to infection by liver trophic virus. Therefore, the core functions of the organ such as regeneration, metabolism, and immunity are closely related to autophagy (Autophagy, 9(8), 1131-1158, 2013). Liver ischemia-reperfusion occurs clinically during liver transplantation, trauma, shock, and elective liver resection. During ischemia-reoxygenation, ROS (reactive oxygen species) and $Ca^{2+}$ levels increase inside mitochondria, which causes mitochondria permeability transition, and oxidative phosphorylation is uncoupled, ultimately inducing apoptosis along with depletion of energy and ATP. Because autophagy proteins are inhibited during anoxia/reoxygenation, the damaged mitochondria are not removed. Therefore, a strategy to activate tolerance to ischemia-reperfusion by activating autophagy has been attempted in preclinical models. Meanwhile, in the acute liver injury model, autophagy is activated to increase cell survival in stress situations.

Liver fibrosis is a common healing response to chronic liver injury of all causes. In order to heal injured tissues, liver tissue deposits new collagen in the wound, but over time, such a process leads to liver cirrhosis. Liver fibrosis is usually associated with chronic liver diseases caused by infections, drugs, metabolic disorders, or autoimmune imbalances. Liver fibrosis caused by the parenchymal cell death and necrosis over a long period of time is associated with inflammatory response, which invites immune cells, activates and accumulates fibrogenic cells, and induces extracellular matrix accumulation. Progression of fibrosis due to continuous liver injury is associated with the expansion of the fibrotic septa and ultimately causes liver cirrhosis.

Liver fibrosis can develop into liver cirrhosis over the next one to ten years and increases a liver-related mortality from 12% to 25% in seven to ten years (Farrell, G. C. & Larter, C. Z. Nonalcoholic fatty liver disease: from steatosis to cirrhosis. Hepatology, 43, S99-S112, 2006). Unfortunately, however, effective clinical therapies are still lacking. Therefore, effective anti-fibrosis therapies are good targets for the treatment of liver diseases. Currently, anti-fibrosis strategies targeting various stages leading to liver fibrosis have been recognized. That is, there are methods of inhibiting the apoptosis of liver cells, or inhibiting liver inflammation, or promoting the apoptosis of fibrogenic cells, or returning phenotype fibrogenic cells to a quiescent state. However, specific drugs used to treat liver fibrosis so far are still limited.

Nonalcoholic fatty liver disease (NAFLD) and nonalcoholic steatohepatitis (NASH) are known as a major cause of the most common chronic liver disease worldwide along with the increase in obesity population, and also known as a disease associated with autophagy regulation. NAFLD can be divided into simple steatosis and NASH. The simple steatosis is considered a benign disease with a clinically favorable prognosis with excessive deposition of fat, but NASH is accompanied by hepatocellular injury and inflammation along with fat deposition, and may cause liver fibrosis, liver cirrhosis, and hepatocellular carcinoma. Thus, when NASH occurs, the 5-year survival rate is reduced to 67% and the 10-year survival rate to 59% (Hepatology, 37, 1202-1219, 2003).

The progression to nonalcoholic steatohepatitis (NASH) in a normal liver is usually described to evolve by way of '2-Hit model'. The stage corresponding to the 1st Hit is the accumulation of fat in the liver, and the 2nd Hit includes oxidative stress, inflammatory response, ER stress, and the like (Gastroenterology, 114, 842-845).

Recent studies have reported that lipids can also be removed through autophagy, and many studies have revealed that autophagy plays an important role in lipid metabolism (Nature, 458, 1131-1135, 2009). However, despite the recent increase in the prevalence rate of NAFLD, there are still no drugs approved as a therapeutic agent of NASH and thus, the available drugs are limited.

Therefore, the present inventors have learned from the above-mentioned prior studies that autophagy plays a crucial role in various diseases, and based on the findings, the inventors have conducted intensive studies to develop a compound that can induce activity of autophagy. As a result, the inventors have found that novel compounds as described below have excellent effects for activating autophagy, and thus can be used as a therapeutic agent for various diseases, in particular, the compounds have activities for inhibiting the progression of liver diseases, thereby completing the present disclosure.

DISCLOSURE

Technical Problem

It is an object of the present disclosure to provide a novel compound and a pharmaceutical composition comprising the same. It is another object of the present disclosure to provide a method for preparing the above-mentioned compound.

Technical Solution

In order to achieve the above objects, there is provided a compound represented by Chemical Formula 1 below, or a pharmaceutically acceptable salt thereof:

[Chemical Formula 1]

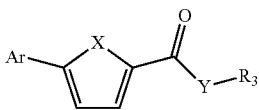

in Chemical Formula 1,
X is O, or S,
Y is O, or NH,
Ar is phenyl, pyridin-3-yl, indolyl, 2-oxoindolyl, quinolinyl, isoquinolinyl, or pyrrolo[2,3-b]pyridinyl,
the Ar is substituted with $R_1$ and $R_2$,
$R_1$ is hydrogen, $C_{1-4}$ alkyl, $C_{1-4}$ alkoxy, hydroxy, halogen, amino, cyano, carboxy, —COO—($C_{1-4}$ alkyl), —CONH—($C_{1-4}$ alkyl), or —CONH-(phenyl),
$R_2$ is hydrogen, $C_{1-4}$ alkyl, $C_{1-4}$ alkoxy, hydroxy, or halogen,
$R_3$ is $C_{1-4}$ alkyl, $C_{6-10}$ aryl, or $C_{6-10}$ heteroaryl containing any one or more heteroatoms selected from the group consisting of N, O and S,
with the proviso that when X is S and Ar is phenyl, both $R_1$ and $R_2$ are not $C_{1-4}$ alkoxy.

Preferably, Y is NH.
Preferably, Ar is phenyl, pyridin-3-yl, indolyl, quinolinyl, or isoquinolinyl, wherein the Ar is substituted with the $R_1$ and $R_2$.
Preferably, $R_1$ is hydrogen, methyl, ethyl, isopropyl, methoxy, ethoxy, hydroxy, fluoro, amino, cyano, carboxy, —COO-(methyl), —CONH-(ethyl), —CONH-(isopropyl), or —CONH-(phenyl).

Preferably, $R_2$ is hydrogen, methyl, methoxy, hydroxy, or fluoro.
Preferably, $R_3$ is ethyl, isopropyl, phenyl, or pyridinyl.
Preferably,
Ar is phenyl,
$R_1$ is $C_{1-4}$ alkyl, $C_{1-4}$ alkoxy, hydroxy, halogen, amino, cyano, carboxy, —COO—($C_{1-4}$ alkyl), —CONH—($C_{1-4}$ alkyl), or —CONH-(phenyl), and
$R_2$ is hydrogen, $C_{1-4}$ alkyl, $C_{1-4}$ alkoxy, hydroxy, or halogen.
Preferably,
Ar is pyridin-3-yl,
$R_1$ is hydrogen, $C_{1-4}$ alkoxy, amino, or cyano, and
$R_2$ is hydrogen, or $C_{1-4}$ alkoxy.
Preferably,
Ar is indoline, quinolinyl, or isoquinolinyl, and
$R_1$ and $R_2$ are hydrogen.
Preferably, X is S, and Y is NH.
Preferably,
Ar is phenyl, pyridin-3-yl, indolyl, quinolinyl, or isoquinolinyl,
$R_1$ is hydrogen, $C_{1-4}$ alkyl, $C_{1-4}$ alkoxy, hydroxy, halogen, amino, or —COO—($C_{1-4}$ alkyl), and
$R_2$ is hydrogen, $C_{1-4}$ alkyl, $C_{1-4}$ alkoxy, or halogen.
Preferably,
Ar is phenyl, or pyridin-3-yl,
$R_1$ is hydrogen, or hydroxy,
$R_2$ is hydrogen, or $C_{1-4}$ alkoxy, and
$R_3$ is $C_{1-4}$ alkyl.
Preferably,
X is O,
Y is O, or NH,
Ar is phenyl, pyridin-3-yl, quinolinyl, or isoquinolinyl,
$R_1$ is hydrogen, $C_{1-4}$ alkyl, hydroxy, cyano, or —COO—($C_{1-4}$ alkyl),
$R_2$ is hydrogen, or $C_{1-4}$ alkyl, and
$R_3$ is $C_{1-4}$ alkyl, or $C_{6-10}$ heteroaryl containing any one or more heteroatoms selected from the group consisting of N, O and S.

Representative examples of the compound represented by Chemical Formula 1 are as follows:
1) 5-(4-hydroxy-3-methoxyphenyl)-N-isopropylthiophene-2-carboxamide,
2) 5-(3-hydroxy-4-methoxyphenyl)-N-isopropylthiophene-2-carboxamide,
3) 5-(3,4-dihydroxyphenyl)-N-isopropylthiophene-2-carboxamide,
4) 5-(3-hydroxyphenyl)-N-isopropylthiophene-2-carboxamide,
5) 5-(4-hydroxyphenyl)-N-isopropylthiophene-2-carboxamide,
6) N-isopropyl-5-(2-methoxypyridin-3-yl)thiophene-2-carboxamide,
7) N-isopropyl-5-(pyridin-3-yl)thiophene-2-carboxamide,
8) N-isopropyl-5-(6-methoxypyridin-3-yl)thiophene-2-carboxamide,
9) 5-(6-ethoxypyridin-3-yl)-N-isopropylthiophene-2-carboxamide,
10) N-isopropyl-5-(5-methoxypyridin-3-yl)thiophene-2-carboxamide,
11) 5-(1H-indol-5-yl)-N-isopropylthiophene-2-carboxamide,
12) 5-(2,6-dimethoxypyridin-3-yl)-N-isopropylthiophene-2-carboxamide,
13) 5-(6-aminopyridin-3-yl)-N-isopropylthiophene-2-carboxamide, 14) 5-(6-amino-5-methoxypyridin-3-yl)-N-isopropylthiophene-2-carboxamide,
15) N-isopropyl-5-(isoquinolin-4-yl)thiophene-2-carboxamide,
16) 5-(6-cyanopyridin-3-yl)-N-isopropylthiophene-2-carboxamide,
17) N-isopropyl-5-(quinolin-3-yl)thiophene-2-carboxamide,
18) 5-(3-aminophenyl)-N-isopropylthiophene-2-carboxamide,
19) methyl 4-(5-(isopropylcarbamoyl)thiophen-2-yl)benzoate,
20) 4-(5-(isopropylcarbamoyl)thiophen-2-yl)benzoic acid,
21) 5-(2-aminophenyl)-N-isopropylthiophene-2-carboxamide,
22) methyl 3-(5-(isopropylcarbamoyl)thiophen-2-yl)benzoate,
23) 3-(5-(isopropylcarbamoyl)thiophen-2-yl)benzoic acid,
24) N-isopropyl-5-p-tolylthiophene-2-carboxamide,
25) 5-(4-ethylphenyl)-N-isopropylthiophene-2-carboxamide,
26) N-isopropyl-5-(4-isopropylphenyl)thiophene-2-carboxamide,
27) 5-(3,4-difluorophenyl)-N-isopropylthiophene-2-carboxamide,
28) 5-(3,5-dimethylphenyl)-N-isopropylthiophene-2-carboxamide,
29) 5-(4-fluorophenyl)-N-isopropylthiophene-2-carboxamide,
30) N-isopropyl-5-m-tolylthiophene-2-carboxamide,
31) 5-(2,4-dimethylphenyl)-N-isopropylthiophene-2-carboxamide,
32) 5-(4-cyanophenyl)-N-isopropylthiophene-2-carboxamide,
33) N-isopropyl-5-(4-(isopropylcarbamoyl)phenyl)thiophene-2-carboxamide,
34) 5-(3,5-difluorophenyl)-N-isopropylthiophene-2-carboxamide,
35) 5-(4-ethoxyphenyl)-N-isopropylthiophene-2-carboxamide,
36) 5-(4-(ethylcarbamoyl)phenyl)-N-isopropylthiophene-2-carboxamide,
37) N-isopropyl-5-(4-(phenylcarbamoyl)phenyl)thiophene-2-carboxamide,
38) 5-(2,4-dimethylphenyl)-N-isopropylfuran-2-carboxamide,
39) 5-(3,4-difluorophenyl)-N-isopropylfuran-2-carboxamide,
40) 5-(4-ethylphenyl)-N-isopropylfuran-2-carboxamide,
41) N-isopropyl-5-m-tolylfuran-2-carboxamide,
42) 5-(4-ethoxyphenyl)-N-isopropylfuran-2-carboxamide,
43) N-isopropyl-5-p-tolylfuran-2-carboxamide,
44) N-isopropyl-5-phenylfuran-2-carboxamide,
45) N-isopropyl-5-(4-isopropylphenyl)furan-2-carboxamide,
46) 5-(4-cyanophenyl)-N-isopropylfuran-2-carboxamide,
47) 5-(3,5-dimethylphenyl)-N-phenylfuran-2-carboxamide,
48) 5-(3,5-dimethylphenyl)-N-phenylthiophene-2-carboxamide,
49) N-phenyl-5-(pyridin-3-yl)thiophene-2-carboxamide,
50) N-ethyl-5-(pyridin-3-yl)thiophene-2-carboxamide,
51) 5-(3,4-difluorophenyl)-N-phenylfuran-2-carboxamide,
52) N-phenyl-5-p-tolylfuran-2-carboxamide,
53) N-phenyl-5-(pyridin-3-yl)furan-2-carboxamide,
54) 5-(4-hydroxy-3-methoxyphenyl)-N-isopropylfuran-2-carboxamide,
55) N,5-di(pyridin-3-yl)thiophene-2-carboxamide,
56) 5-(4-hydroxy-3-methoxyphenyl)-N-phenylfuran-2-carboxamide,
57) 5-(3,4-dimethoxyphenyl)-N-(pyridin-3-yl)furan-2-carboxamide,
58) N,5-di(pyridin-3-yl)furan-2-carboxamide,
59) 5-(4-hydroxy-3-methoxyphenyl)-N-(pyridin-3-yl)furan-2-carboxamide,
60) 5-(4-hydroxy-3-methoxyphenyl)-N-(pyridin-3-yl)thiophene-2-carboxamide,
61) 5-(2-aminophenyl)-N-isopropylfuran-2-carboxamide,
62) N-isopropyl-5-(quinolin-3-yl)furan-2-carboxamide,
63) N-isopropyl-5-(2-oxoindolin-5-yl)furan-2-carboxamide,
64) 5-(1H-indol-5-yl)-N-isopropylfuran-2-carboxamide,
65) N-isopropyl-5-(isoquinolin-4-yl)furan-2-carboxamide,
66) N-isopropyl-5-(pyridin-3-yl)furan-2-carboxamide,
67) isopropyl 5-(pyridin-3-yl)furan-2-carboxylate,
68) ethyl 5-(pyridin-3-yl)furan-2-carboxylate,
69) phenyl 5-(pyridin-3-yl)furan-2-carboxylate,
70) pyridin-3-yl 5-(pyridin-3-yl)furan-2-carboxylate,
71) ethyl 5-(pyridin-3-yl)thiophene-2-carboxylate,
72) isopropyl 5-(pyridin-3-yl)thiophene-2-carboxylate,
73) phenyl 5-(pyridin-3-yl)thiophene-2-carboxylate,
74) pyridin-3-yl 5-(pyridin-3-yl)thiophene-2-carboxylate,
75) 5-(3-hydroxyphenyl)-N-isopropylfuran-2-carboxamide,
76) 5-(3,4-dimethoxyphenyl)-N-isopropylfuran-2-carboxamide,
77) ethyl 5-(3,4-dimethoxyphenyl)furan-2-carboxylate,
78) 5-(3,5-difluorophenyl)-N-isopropylfuran-2-carboxamide,
79) ethyl 5-(2-aminophenyl)furan-2-carboxylate,
80) ethyl 5-(isoquinolin-4-yl)furan-2-carboxylate,
81) ethyl 5-(4-(methoxycarbonyl)phenyl)furan-2-carboxylate,
82) ethyl 5-(3,5-difluorophenyl)furan-2-carboxylate,
83) 5-(3,5-dimethylphenyl)-N-(pyridin-3-yl)furan-2-carboxamide,
84) 5-(2,4-dimethylphenyl)-N-(pyridin-3-yl)furan-2-carboxamide,
85) 5-(3,5-dimethylphenyl)-N-isopropylfuran-2-carboxamide,
86) ethyl 5-(3,5-dimethylphenyl)furan-2-carboxylate,
87) ethyl 5-(3-hydroxyphenyl)furan-2-carboxylate,
88) ethyl 5-(quinolin-3-yl)furan-2-carboxylate,
89) ethyl 5-(4-cyanophenyl)furan-2-carboxylate,
90) ethyl 5-(1H-indol-5-yl)furan-2-carboxylate,
91) 5-(3-hydroxyphenyl)-N-(pyridin-3-yl)furan-2-carboxamide,
92) 5-(3-(ethylcarbamoyl)phenyl)-N-isopropylfuran-2-carboxamide,
93) 5-(4-(ethylcarbamoyl)phenyl)-N-isopropylfuran-2-carboxamide, and
94) N-isopropyl-5-(4-(isopropylcarbamoyl)phenyl)furan-2-carboxamide.

In addition, if necessary, the compound represented by Chemical Formula 1 can be prepared in the form of a pharmaceutically acceptable salt using conventional methods in the technical field to which the present disclosure pertains. In one example, a pharmaceutically acceptable metal salt can be obtained using a base by a conventional method, and examples of the metal salt include a sodium salt, a potassium salt, or a calcium salt. In another example, an acid addition salt formed by a pharmaceutically acceptable free acid is useful. As the free acid, an inorganic acid and an organic acid can be used. As the inorganic acid, hydrochloric acid, bromic acid, sulfuric acid, phosphoric acid and the like can be used. As the organic acid, citric acid, acetic acid, lactic acid, maleic acid, gluconic acid, methanesulfonic acid, succinic acid, 4-toluenesulfonic acid, glutamic acid, aspartic acid, or the like can be used.

The compound represented by Chemical Formula 1 according to the present disclosure includes not only pharmaceutically acceptable salts thereof, but also enantiomers, solvates and hydrates that can be prepared therefrom. The enantiomers, solvates and hydrates of the compound represented by Chemical Formula 1 can be prepared from the compound represented by Chemical Formula 1 using a conventional method in the technical field to which the present disclosure pertains.

Further, the compound represented by Chemical Formula 1 according to the present disclosure may be prepared either in a crystalline form or in a non-crystalline form, and when the compound of Chemical Formula 1 is prepared in a crystalline form, it may be optionally hydrated or solvated. In the present disclosure, the compound of Chemical Formula 1 may not only include a stoichiometric hydrate, but also include a compound containing various amounts of water. The solvate of the compound of Chemical Formula 1 according to the present disclosure includes both stoichiometric solvates and non-stoichiometric solvates.

Further, according to the present disclosure, the compound represented by Chemical Formula 1 can be prepared by the method as shown in Reaction Scheme 1 below:

[Reaction Scheme 1]

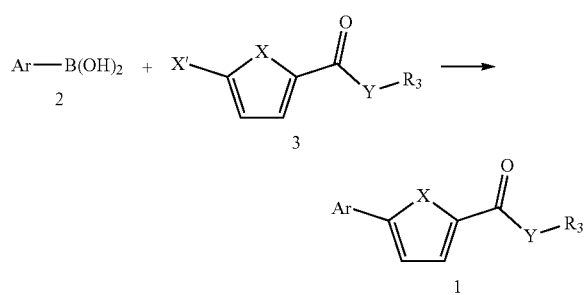

in Reaction Scheme 1, X, Y, Ar, $R_1$, $R_2$, and $R_3$ are as defined above, and X' is halogen, more preferably bromo or chloro.

The above reaction is a Suzuki coupling reaction, and a reactive group for the Suzuki coupling reaction can be changed. Also, the reaction is preferably carried out in the presence of palladium catalyst. Further, the reaction molar ratio of the compound represented by Chemical Formula 2 and the compound represented by Chemical Formula 3 is preferably 10:1 to 1:10. Further, the reaction is preferably performed at 20 to 200° C., and the reaction is preferably performed for 10 minutes to 10 hours. After the reaction, a purification process may be included if necessary. The above preparation method can be more embodied in the Examples to be described below.

Further, the present disclosure provides a pharmaceutical composition for preventing or treating autophagy-related diseases, comprising the compound represented by Chemical Formula 1 or a pharmaceutically acceptable salt thereof.

The compound represented by Chemical Formula 1 according to the present disclosure, or a pharmaceutically acceptable salt thereof can increase the autophagy activity, and thus can be valuably used for preventing or treating diseases associated with autophagy regulation. Examples of the diseases associated with autophagy regulation include metabolic diseases such as liver disease, obesity, diabetes, and atherosclerosis, degenerative brain diseases such as age-related macular degeneration, dementia, and Parkinson's disease, pulmonary fibrosis and inflammatory bowel disease, etc. Further, examples of the liver diseases include liver fibrosis, liver cirrhosis, hepatitis, alcoholic liver disease, non-alcoholic fatty liver disease, or non-alcoholic steatohepatitis (NASH).

As used herein, the term "prevention" refers to any act to delay or inhibit occurrence, spread or recurrence of the autophagy-related diseases by administration of the composition of the present disclosure, and the term "treatment" refers to any act to improve or change the symptoms of the above diseases for the better by administration of the composition of the present disclosure.

The pharmaceutical composition according to the present disclosure can be formulated in types for oral or parenteral administrations according to a standard pharmaceutical practice. These formulations may contain additives such as pharmaceutically acceptable carrier, adjuvant or diluent in addition to the active ingredient. Suitable carriers include, for example, physiological saline, polyethylene glycol, ethanol, vegetable oil, isopropyl myristate and the like. Diluents include, for example, lactose, dextrose, sucrose, mannitol, sorbitol, cellulose and/or glycine and the like, but are not limited thereto. Further, the compounds of the present disclosure can be dissolved in oils, propylene glycol or other solvents commonly used in the preparation of injection solutions. Furthermore, the compounds of the present disclosure can be formulated in ointments or creams for topical application.

A preferred dose of the compound represented by Chemical Formula 1 according to the present disclosure may be varied according to the condition and weight of a patient, the severity of a disease, the type of a drug, and the route and duration of administration, but it may be suitably selected by those skilled in the art. In order to achieve the desirable effects, however, the compound represented by Chemical Formula 1 according to the present disclosure may be administrated daily at a dose of 0.0001 to 100 mg/kg (body weight), and preferably 0.001 to 100 mg/kg (body weight). The administration may be performed once a day or in divided doses each day through an oral or parenteral route.

Depending on the method of administration, the pharmaceutical composition according to the present disclosure may contain the compound represented by Chemical Formula 1 according to the present disclosure or a pharmaceutically acceptable salt thereof in an amount of 0.001 to 99% by weight, preferably 0.01 to 60% by weight.

The pharmaceutical composition of the present disclosure may be administered to mammals such as a rat, a mouse, a domestic animal and a human, through various routes. The administration may be carried out through all possible methods, for example, oral, rectal, intravenous, intramuscular, subcutaneous, intra-endometrial, intracerebroventricular injection.

Advantageous Effects

The compound according to the present disclosure or a pharmaceutically acceptable salt thereof exhibits effects for activating autophagy, and thus can be valuably used for preventing or treating diseases associated with autophagy regulation, including metabolic diseases such as liver disease, obesity, diabetes, and atherosclerosis, degenerative brain diseases such as age-related macular degeneration, dementia, and Parkinson's disease, pulmonary fibrosis and inflammatory bowel disease, etc.

DETAILED DESCRIPTION OF THE EMBODIMENTS

Figure 1:
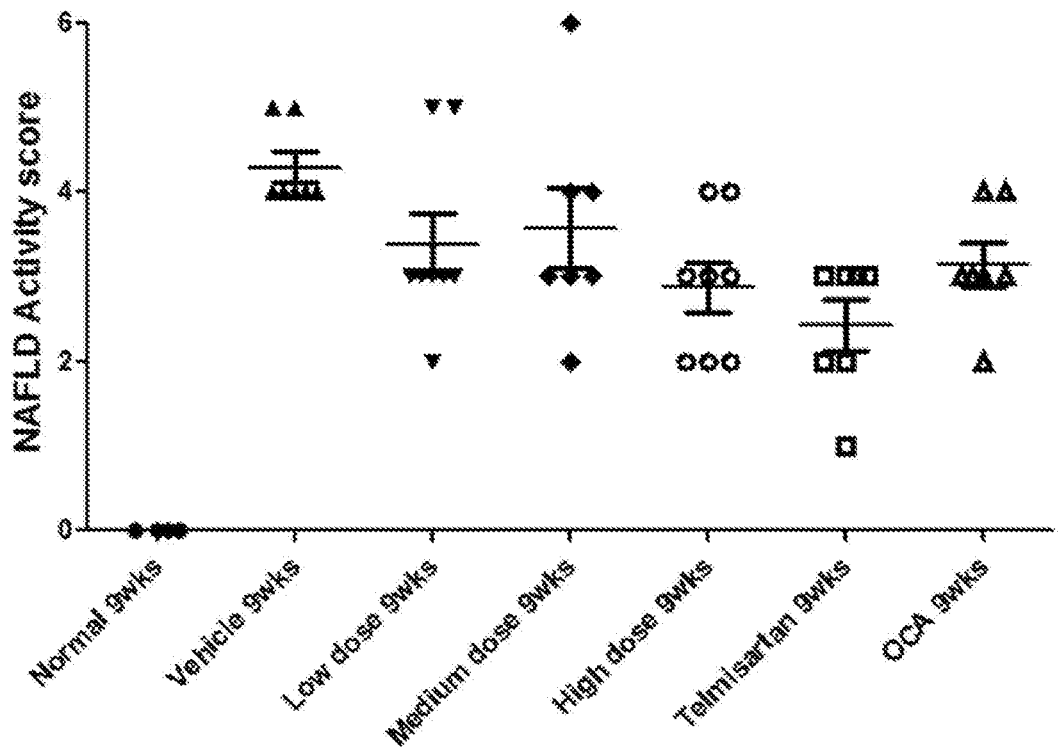
FIG. 1 is a graph showing the nonalcoholic fatty liver disease (NAFLD) activity score calculated from a composite score of steatosis, inflammation and ballooning in the liver of experimental animals.

Below, the present disclosure will be described in more detail by way of examples. However, these examples are provided for illustrative purposes only, and should not be construed as limiting the scope of the present disclosure to these examples.

PREPARATION EXAMPLE

Preparation Example 1: Preparation of Intermediate 1

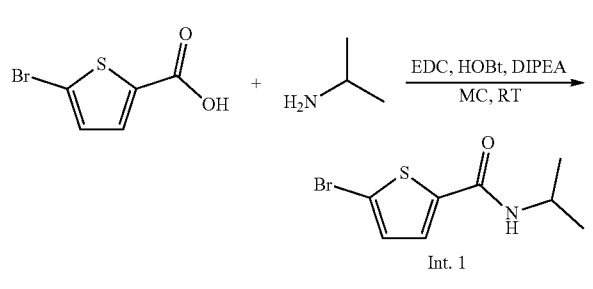

Isopropylamine (29.0 mmol), 5-brothiophene-2-carboxylic acid (9.66 mmol), EDC (14.5 mmol), HOBT (14.5 mmol), and diisopropylamine (29.0 mmol) were added to dichloromethane (20 mL), and the mixture was stirred at room temperature for 10 hours. The organic solvent was concentrated under reduced pressure, purified by flash column chromatography (n-Hx:EtOAc=5:1), and then recrystallized using dichloromethane and hexane. The product was dried by a vacuum pump to give Intermediate 1 as a white solid (yield: 59.70%).

Preparation Example 2: Preparation of Intermediate 2

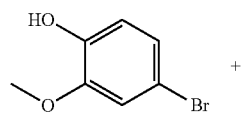

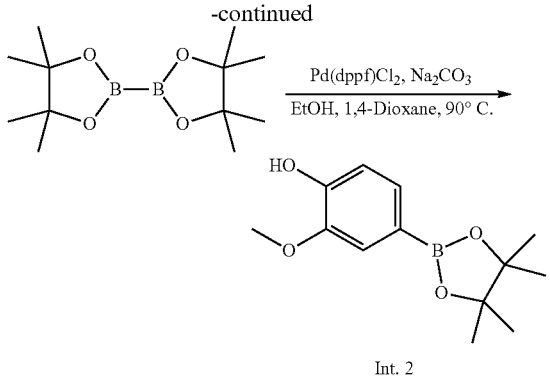

4-Bromo-2-methoxyphenol (1.0 g, 4.93 mmol), 4,4,4',4',5,5,5',5'-octamethyl-2,2'-bi(1,3,2-dioxaborolane) (1.376 g, 5.42 mmol), [1,1'-bis(diphenylphosphino)ferrocene]dichloropalladium(II) dichloromethane (241.0 mg, 0.296 mmol), and calcium carbonate (2.042 g, 14.8 mmol) were added to 1,4-dioxane (40.0 mL), and the mixture was stirred at 90° C. for 16 hours. The organic solvent was concentrated under reduced pressure, and purified by flash column chromatography (n-Hx:EtOAc=7:1), and then dried by a vacuum pump to give Intermediate 2 as an oil (yield: 66.70%).

Preparation Example 3: Preparation of Intermediate 3

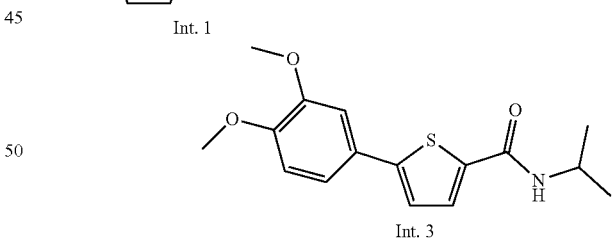

5-Bromo-N-isopropylthiophene-2-carboxamide (Intermediate 1, 2.015 mmol), 2M sodium carbonate aqueous solution (0.64 mL, 1.29 mmol) and dichlorobis(triphenylphosphine)palladium(II) (22.6 mg, 0.032 mmol) were added to 1,2-dimethoxyethane (3 mL), and the mixture was stirred at room temperature for 30 minutes. (3,4-Dimethoxyphenyl)boronic acid (3.022 mmol) was dissolved in ethanol (3 mL) and then added to the above solution. The mixture was stirred at 80° C. for 6 hours, and extracted twice with dichloromethane. The extracted solution was dehydrated with anhydrous magnesium sulfate, and the organic solvent was concentrated under reduced pressure, purified by flash column chromatography (n-Hx:EtOAc=3:1) and then dried by a vacuum pump to give Intermediate 3 as a white solid (yield: 66.70%).

Preparation Example 4: Preparation of Intermediate 4

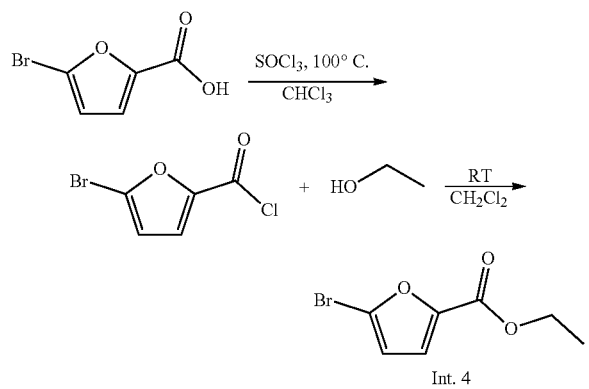

Thionyl chloride (1.14 mL, 15.7 mmol) and 5-bromo-furan-2-carboxylic acid (5.24 mmol) were added to chloroform (30 mL), and the mixture was stirred at 100° C. for 4 hours. The organic solvent was concentrated under reduced pressure, and ethyl alcohol (15 mL) was added to dichloromethane (15 mL), and the mixture was stirred at room temperature for 2 hours. The organic solvent was concentrated under reduced pressure, purified by flash column chromatography (n-Hx:EtOAc=5:1), and then dried by a vacuum pump to give Intermediate 4 as an oil (yield: 95.1%).

EXAMPLE

Example 1: Preparation of 5-(4-hydroxy-3-methoxyphenyl)-N-isopropylthiophene-2-carboxamide

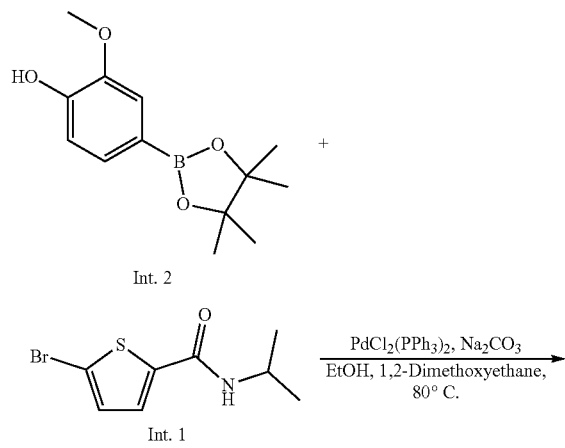

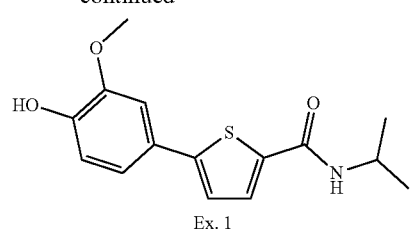

The title compound (yield: 72.83%) was obtained as a white solid in the same manner as in Preparation Example 3, except that Intermediate 2 was used instead of (3,4-dimethoxyphenyl) boronic acid.

$^1$H NMR (400 MHz, DMSO-$d_6$) δ 9.34 (s, 1H), 8.17 (d, 1H, J=8.0 Hz), 7.72 (d, 1H, J=3.6 Hz), 7.37 (d, 1H, J=4.0 Hz), 7.20 (s, 1H), 7.11-7.10 (m, 1H), 6.82-6.80 (m, 1H), 4.09-4.02 (m, 1H), 3.84 (s, 3H), 1.16 (d, 6H, J=6.8 Hz).

Example 2: Preparation of 5-(3-hydroxy-4-methoxyphenyl)-N-isopropylthiophene-2-carboxamide

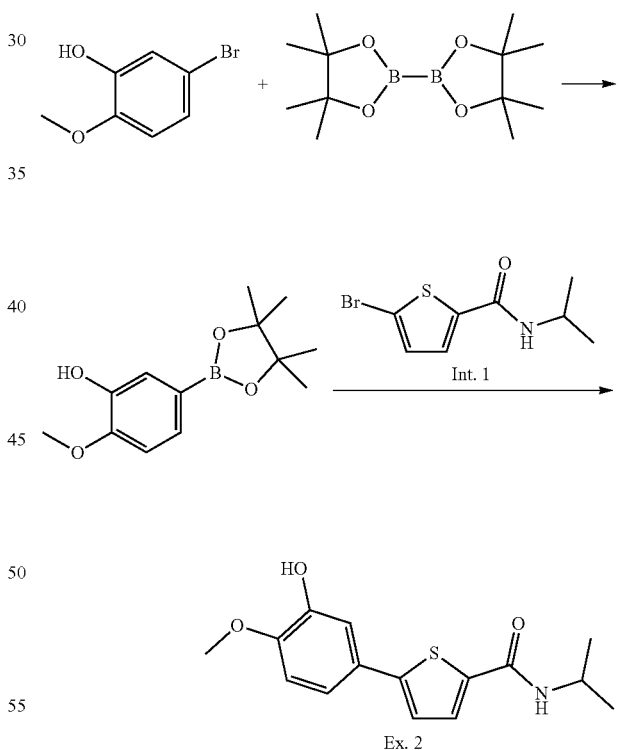

The title compound (yield: 36.96%) was obtained as a white solid in the same manner as in Preparation Examples 2 and 3, except that 5-bromo-2-methoxyphenol was used instead of 4-bromo-2-methoxyphenol.

$^1$H NMR (400 MHz, DMSO-$d_6$) δ 9.26 (s, 1H), 8.19 (d, 1H, J=7.6 Hz), 7.71 (d, 1H, J=4.0 Hz), 7.31 (d, 1H, J=4.0 Hz), 7.12-7.09 (m, 2H), 6.98-6.96 (m, 1H), 4.09-4.00 (m, 1H), 3.80 (s, 3H), 1.16 (d, 6H, J=6.8 Hz).

Example 3: Preparation of 5-(3,4-dihydroxyphenyl)-N-isopropylthiophene-2-carboxamide

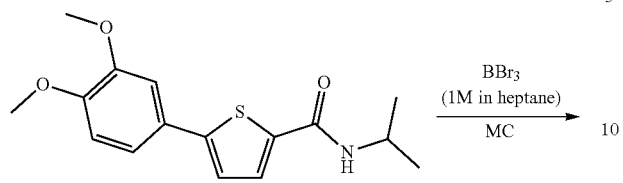

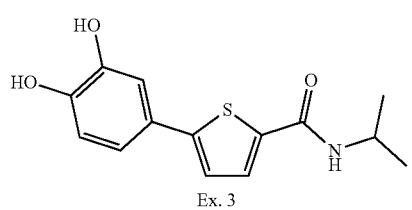

5-(3,4-Dimethoxyphenyl)-N-isopropylthiophen-2-carboxamide (100 mg, 0.327 mmol) was put in a 50.0 ml round-bottom flask, and after argon replacement, dichloromethane (3.46 ml) and 1M boron tribromide heptane solution (3.93 ml) were added thereto at 0° C. After stirring for 30 hours, methanol was added to terminate the reaction, and the reaction mixture was concentrated under reduced pressure. It was then purified by flash column chromatography (10% MeOH in MC), and then dried by a vacuum pump to give the title compound as a white solid (yield: 20.05%).

$^1$H NMR (300 MHz, DMSO-$d_6$) δ 9.23 (s, 2H), 8.16 (d, 1H, J=7.8 Hz), 7.69 (d, 1H, J=3.9 Hz), 7.24 (d, 1H, J=3.9 Hz), 7.04 (d, 1H, J=2.4 Hz), 7.00-6.97 (m, 1H), 6.79-6.76 (m, 1H), 4.10-3.99 (m, 1H) 1.16 (d, 6H, J=6.6 Hz).

Example 4: Preparation of 5-(3-hydroxyphenyl)-N-isopropylthiophene-2-carboxamide

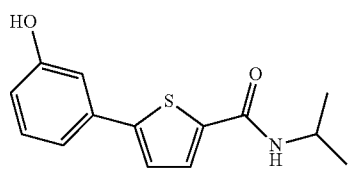 [SMILES: CC(C)NC(=O)c1ccc(-c2cccc(O)c2)s1]

The title compound (yield: 57.90%) was obtained as a white solid in the same manner as in Preparation Example 3, except that (3-hydroxyphenyl)boronic acid was used instead of (3,4-dimethoxyphenyl)boronic acid.

$^1$H NMR (300 MHz, DMSO-$d_6$) δ 9.66 (s, 1H), 8.25 (d, 1H, J=7.8 Hz), 7.75 (d, 1H, J=3.9 Hz), 7.43 (d, 1H, J=3.9 Hz), 7.26-7.21 (m, 1H), 7.14-7.11 (m, 1H), 7.06-7.04 (m, 1H), 6.78-6.75 (m, 1H), 4.11-4.00 (m, 1H), 1.17 (d, 6H, J=6.6 Hz).

Example 5: Preparation of 5-(4-hydroxyphenyl)-N-isopropylthiophene-2-carboxamide

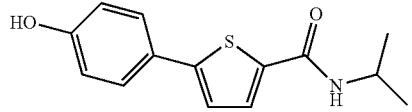 [SMILES: CC(C)NC(=O)c1ccc(-c2ccc(O)cc2)s1]

The title compound (yield: 11.80%) was obtained as a white solid in the same manner as in Preparation Example 3, except that (4-hydroxyphenyl)boronic acid was used instead of (3,4-dimethoxyphenyl)boronic acid.

$^1$H NMR (300 MHz, DMSO-$d_6$) δ 9.80 (s, 1H), 8.19 (d, 1H, J=7.8 Hz), 7.71 (d, 1H, J=3.9 Hz), 7.52 (d, 2H, J=8.7 Hz), 7.32 (d, 1H, J=3.9 Hz), 6.82 (d, 2H, J=8.7 Hz), 4.08-4.01 (m, 1H), 1.16 (d, 6H, J=6.6 Hz).

Example 6: Preparation of N-isopropyl-5-(2-methoxypyridin-3-yl)thiophene-2-carboxamide

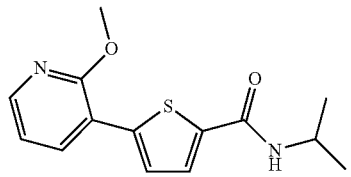 [SMILES: COc1ncccc1-c1ccc(C(=O)NC(C)C)s1]

The title compound (yield: 46.30%) was obtained as a white solid in the same manner as in Preparation Example 3, except that (2-methoxypyridin-3-yl)boronic acid was used instead of (3,4-dimethoxyphenyl)boronic acid.

$^1$H NMR (300 MHz, DMSO-$d_6$) δ 8.27 (d, 1H, J=10.4 Hz), 8.23-8.17 (m, 2H), 7.78 (d, 1H, J=5.2 Hz), 7.71 (d, 1H, J=5.6 Hz), 7.14-7.10 (m, 1H), 4.10-4.03 (m, 4H) 1.17 (d, 6H, J=9.2 Hz).

Example 7: Preparation of N-isopropyl-5-(pyridin-3-yl)thiophene-2-carboxamide

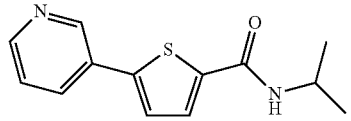 [SMILES: CC(C)NC(=O)c1ccc(-c2cccnc2)s1]

The title compound (yield: 64.52%) was obtained as a white solid in the same manner as in Preparation Example 3, except that pyridine-3-ylboronic acid was used instead of (3,4-dimethoxyphenyl)boronic acid.

$^1$H NMR (400 MHz, DMSO-$d_6$) δ 8.95 (d, 1H, J=2.0 Hz), 8.56 (d, 1H, J=4.4 Hz), 8.10 (d, 1H, J=8.0 Hz), 7.66 (d, 1H, J=4.0 Hz), 7.48 (q, 1H, J=4.8 Hz), 4.12-4.03 (m, 1H), 1.19 (d, 6H, J=6.4 Hz)

Example 8: Preparation of N-isopropyl-5-(6-methoxypyridin-3-yl)thiophene-2-carboxamide

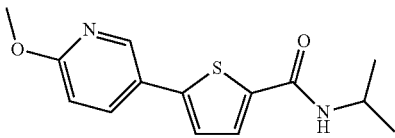 [SMILES: COc1ccc(-c2ccc(C(=O)NC(C)C)s2)cn1]

The title compound (yield: 72.83%) was obtained as a white solid in the same manner as in Preparation Example 3, except that (6-methoxypyridin-3-yl)boronic acid was used instead of (3,4-dimethoxyphenyl)boronic acid.

$^1$H NMR (400 MHz, DMSO-$d_6$) δ 8.54 (d, 1H, J=2.4 Hz), 8.27 (d, 1H, J=7.6 Hz), 8.03 (dd, 1H, Ja=8.8 Hz Jb=2.4 Hz), 7.79 (d, 1H, J=4.0 Hz), 7.49 (d, 1H, J=4.0 Hz), 6.91 (d, 1H, J=8.8 Hz), 4.11-4.03 (m, 1H), 3.90 (s, 3H), 1.19 (d, 6H, J=6.4 Hz)

Example 9: Preparation of 5-(6-ethoxypyridin-3-yl)-N-isopropylthiophene-2-carboxamide

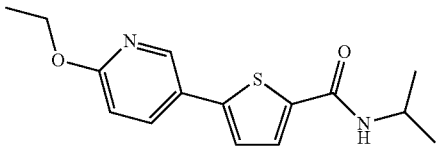 [SMILES: CCOc1ccc(-c2ccc(C(=O)NC(C)C)s2)cn1]

The title compound (yield: 51.23%) was obtained as a white solid in the same manner as in Preparation Example 3, except that (6-ethoxypyridin-3-yl)boronic acid was used instead of (3,4-dimethoxyphenyl)boronic acid.

$^1$H NMR (400 MHz, DMSO-$d_6$) δ 8.51 (d, 1H, J=2.4 Hz), 8.27 (d, 1H, J=8.0 Hz), 8.01 (dd, 1H, Ja=8.4 Hz, Jb=2.4 Hz), 7.78 (d, 1H, J=4.0 Hz), 7.48 (d, 1H, J=4.0 Hz), 6.87 (d, 1H, J=8.8 Hz), 4.34 (q, 2H, J=7.2 Hz), 4.11-4.03 (m, 1H), 1.34 (t, 3H, J=7.0 Hz), 1.18 (d, 6H, J=6.8 Hz)

Example 10: Preparation of N-isopropyl-5-(5-methoxypyridin-3-yl)thiophene-2-carboxamide

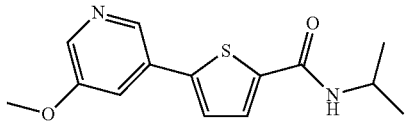 [SMILES: COc1cncc(-c2ccc(C(=O)NC(C)C)s2)c1]

The title compound (yield: 75.10%) was obtained as a white solid in the same manner as in Preparation Example 3, except that (5-methoxypyridin-3-yl)boronic acid was used instead of (3,4-dimethoxyphenyl)boronic acid.

$^1$H NMR (300 MHz, DMSO-$d_6$) δ 8.52 (s, 1H), 8.33-8.27 (m, 2H), 7.82 (d, 1H, J=3.6 Hz), 7.69 (d, 1H, J=4.0 Hz), 7.65 (s, 1H), 4.09-4.04 (m, 1H), 3.91 (s, 3H), 1.18 (d, 6H, J=6.8 Hz).

Example 11: Preparation of 5-(1H-indol-5-yl)-N-isopropylthiophene-2-carboxamide

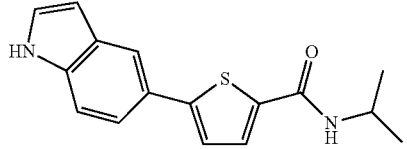 [SMILES: CC(C)NC(=O)c1ccc(-c2ccc3[nH]ccc3c2)s1]

The title compound (yield: 44.40%) was obtained as a white solid in the same manner as in Preparation Example 3, except that (1H-indol-5-yl)boronic acid was used instead of (3,4-dimethoxyphenyl)boronic acid.

$^1$H NMR (300 MHz, DMSO-$d_6$) δ 11.24 (s, 1H), 8.20 (d, 1H, J=7.8 Hz), 7.76 (d, 1H, J=3.9 Hz), 7.69-7.68 (m, 1H), 7.59 (d, 1H, J=8.1 Hz), 7.45-7.41 (m, 2H), 7.37-7.34 (m, 1H), 6.46-6.45 (m, 1H), 4.10-4.03 (m, 1H), 1.18 (d, 6H, J=6.6 Hz).

Example 12: Preparation of 5-(2,6-dimethoxypyridin-3-yl)-N-isopropylthiophene-2-carboxamide

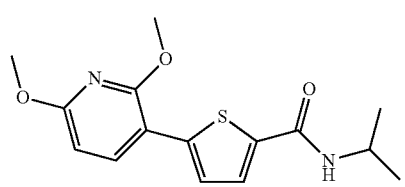 [SMILES: COc1ccc(-c2ccc(C(=O)NC(C)C)s2)c(OC)n1]

The title compound (yield: 50.30%) was obtained as a white solid in the same manner as in Preparation Example 3, except that (2,6-dimethoxypyridin-3-yl)boronic acid was used instead of (3,4-dimethoxyphenyl)boronic acid.

$^1$H NMR (400 MHz, DMSO-$d_6$) δ 8.12 (d, 1H, J=11.2 Hz), 7.73 (d, 1H, J=5.2 Hz), 7.53 (d, 1H, J=5.2 Hz), 6.51 (d, 1H, J=11.2 Hz), 4.09-4.00 (m, 4H), 3.92 (s, 3H), 1.17 (d, 6H, J=8.8 Hz)

Example 13: Preparation of 5-(6-aminopyridin-3-yl)-N-isopropylthiophene-2-carboxamide

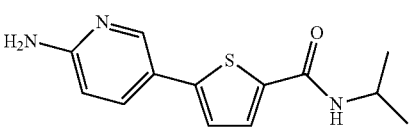 [SMILES: CC(C)NC(=O)c1ccc(-c2ccc(N)nc2)s1]

The title compound (yield: 52.80%) was obtained as a white solid in the same manner as in Preparation Example 3, except that (6-aminopyridin-3-yl) boronic acid was used instead of (3,4-dimethoxyphenyl)boronic acid.

$^1$H NMR (400 MHz, DMSO-$d_6$) δ 8.27 (dd, 1H, Ja=3.6 Hz, Jb=0.8 Hz), 8.16 (d, 1H, J=10.8 Hz), 7.71-7.66 (m, 2H), 7.29 (d, 1H, J=5.2 Hz), 6.51-6.48 (m, 1H), 6.28 (s, 2H), 4.08-4.01 (m, 1H), 1.16 (d, 6H, J=8.0 Hz)

Example 14: Preparation of 5-(6-amino-5-methoxy-pyridin-3-yl)-N-isopropylthiophene-2-carboxamide

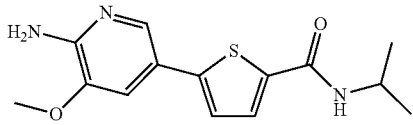 [SMILES: COc1cc(-c2ccc(C(=O)NC(C)C)s2)cnc1N]

The title compound (yield: 64.30%) was obtained as a white solid in the same manner as in Preparation Example 3, except that (6-amino-5-methoxypyridin-3-yl)boronic acid was used instead of (3,4-dimethoxyphenyl)boronic acid.

$^1$H NMR (400 MHz, DMSO-$d_6$) δ 8.161 (d, 1H, J=10.4 Hz), 7.88 (d, 1H, J=2.4 Hz), 7.72 (d, 1H, J=5.6 Hz), 7.37 (d, 1H, J=5.2 Hz), 7.27 (d, 1H, J=2.4 Hz), 6.08 (s, 2H), 4.11-3.99 (m, 1H), 3.87 (s, 3H), 1.164 (d, 6H, J=8.8 Hz)

Example 15: Preparation of N-isopropyl-5-(isoquinolin-4-yl)thiophene-2-carboxamide

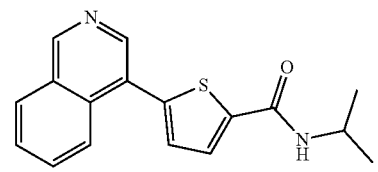 [SMILES: CC(C)NC(=O)c1ccc(-c2cncc3ccccc23)s1]

The title compound (yield: 54.80%) was obtained as a white solid in the same manner as in Preparation Example 3, except that isoquinoline-4-ylboronic acid was used instead of (3,4-dimethoxyphenyl)boronic acid.

$^1$H NMR (300 MHz, DMSO-$d_6$) δ 9.38 (d, 1H, J=0.9 Hz), 8.60 (s, 1H), 8.40 (d, 1H, J=7.5 Hz), 8.27-8.20 (m, 2H), 7.94-7.87 (m, 2H), 7.82-7.77 (m, 1H), 7.46 (d, 1H, J=3.9 Hz), 4.16-4.05 (m, 1H), 1.21 (d, 6H, J=6.6 Hz).

Example 16: Preparation of 5-(6-cyanopyridin-3-yl)-N-isopropylthiophene-2-carboxamide

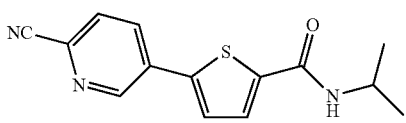 [SMILES: CC(C)NC(=O)c1ccc(-c2ccc(C#N)nc2)s1]

The title compound was obtained as a white solid in the same manner as in Preparation Example 3, except that 6-cyanopyridin-3-ylboronic acid was used instead of (3,4-dimethoxyphenyl)boronic acid.

$^1$H NMR (300 MHz, DMSO-$d_6$) δ 9.14-9.13 (m, 1H), 8.40 (d, 1H, J=7.8 Hz), 8.36-8.31 (m, 1H), 8.11-8.08 (m, 1H), 7.86 (s, 2H), 4.12-4.01 (m, 1H), 1.18 (d, 6H, J=6.6 Hz).

Example 17: Preparation of N-isopropyl-5-(quinolin-3-yl)thiophene-2-carboxamide

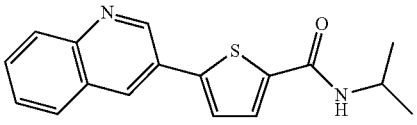 [SMILES: CC(C)NC(=O)c1ccc(-c2cnc3ccccc3c2)s1]

The title compound (yield: 62.40%) was obtained as a white solid in the same manner as in Preparation Example 3, except that quinoline-3-ylboronic acid was used instead of (3,4-dimethoxyphenyl)boronic acid.

$^1$H NMR (300 MHz, DMSO-$d_6$) δ 9.30 (d, 1H, J=2.4 Hz), 8.67 (d, 1H, J=2.1 Hz), 8.38-8.32 (m, 1H), 8.07-8.03 (m, 2H), 7.87 (d, 1H, J=3.9 Hz), 7.82-7.74 (m, 2H), 7.69-7.63 (m, 1H), 4.12-4.03 (m, 1H), 1.19 (d, 6H, J=6.6 Hz).

Example 18: Preparation of 5-(3-aminophenyl)-N-isopropylthiophene-2-carboxamide

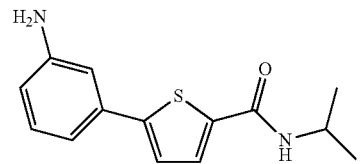 [SMILES: CC(C)NC(=O)c1ccc(-c2cccc(N)c2)s1]

The title compound (yield: 24.20%) was obtained as a white solid in the same manner as in Preparation Example 3, except that (3-aminophenyl)boronic acid was used instead of (3,4-dimethoxyphenyl)boronic acid.

$^1$H NMR (300 MHz, DMSO-$d_6$) δ 8.22 (d, 1H, J=7.8 Hz), 7.73 (d, 1H, J=3.9 Hz), 7.34 (d, 1H, J=4.2 Hz), 7.07 (t, 1H, J=7.7 Hz), 6.87-6.82 (m, 2H), 6.57-6.54 (m, 1H), 5.25 (s, 2H), 4.11-3.99 (m, 1H), 1.17 (d, 6H, J=6.6 Hz).

Example 19: Preparation of methyl 4-(5-(isopropylcarbamoyl)thiophen-2-yl)benzoate

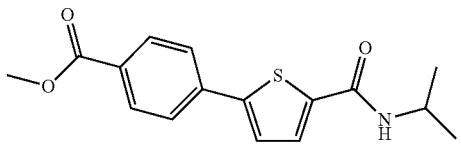 [SMILES: COC(=O)c1ccc(-c2ccc(C(=O)NC(C)C)s2)cc1]

The title compound (yield: 11.90%) was obtained as a white solid in the same manner as in Preparation Example 3, except that (4-(methoxycarbonyl)phenyl)boronic acid was used instead of (3,4-dimethoxyphenyl)boronic acid.

$^1$H NMR (300 MHz, DMSO-$d_6$) δ 8.33 (d, 1H, J=7.8 Hz), 8.03-7.99 (m, 2H), 7.88-7.84 (m, 2H), 7.82 (d, 1H, J=3.9 Hz), 7.69 (d, 1H, J=3.9 Hz), 4.10-4.03 (m, 1H), 3.87 (s, 3H), 1.18 (d, 6H, J=6.6 Hz).

Example 20: Preparation of 4-(5-(isopropylcarbamoyl)thiophen-2-yl)benzoic acid

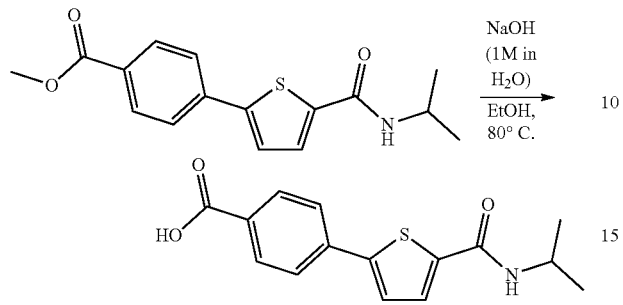

Methyl 4-(5-(isopropylcarbamoyl)thiophen-2-yl)benzoate (100.0 mg, 0.342 mmol) was added to 1M sodium hydroxide aqueous solution (3.0 ml) and ethanol (3.0 ml), and the mixture was stirred at 80° C. for 2 hours. The reaction temperature was lowered to room temperature, and a 5% hydrochloric acid solution was added until pH 2 was reached. The formed suspension was filtered using a filter, purified by flash column chromatography (n-Hx:EtOAc=3:1), and then dried by a vacuum pump to give the title compound as a white solid (yield 29.40%).

$^1$H NMR (300 MHz, DMSO-$d_6$) δ 8.33 (d, 1H, J=7.8 Hz), 7.99 (d, 2H, J=8.4 Hz), 7.84-7.81 (m, 3H), 7.67 (d, 1H, J=3.9 Hz), 4.12-4.01 (m, 1H), 1.18 (d, 6H, J=6.6 Hz).

Example 21: Preparation of 5-(2-aminophenyl)-N-isopropylthiophene-2-carboxamide

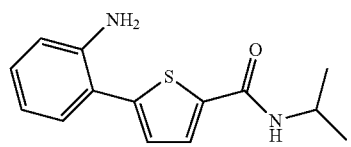 [SMILES: CC(C)NC(=O)c1ccc(-c2ccccc2N)s1]

The title compound (yield: 3.73%) was obtained as a white solid in the same manner as in Preparation Example 3, except that (2-aminophenyl)boronic acid was used instead of (3,4-dimethoxyphenyl)boronic acid.

$^1$H NMR (300 MHz, DMSO-$d_6$) δ 8.22 (d, 1H, J=7.8 Hz), 7.77 (d, 1H, J=3.9 Hz), 7.24 (d, 1H, J=3.9 Hz), 7.20-7.17 (m, 1H), 7.10-7.05 (m, 1H), 6.82-6.79 (m, 1H), 6.65-6.60 (m, 1H), 5.16 (s, 2H), 4.12-4.01 (m, 1H), 1.17 (d, 6H, J=6.6 Hz).

Example 22: Preparation of methyl 3-(5-(isopropylcarbamoyl)thiophen-2-yl)benzoate

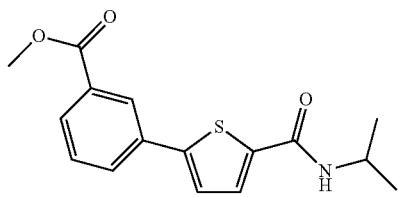 [SMILES: COC(=O)c1cccc(-c2ccc(C(=O)NC(C)C)s2)c1]

The title compound (yield: 22.30%) was obtained as a white solid in the same manner as in Preparation Example 3, except that (3-(methoxycarbonyl)phenyl)boronic acid was used instead of (3,4-dimethoxyphenyl)boronic acid.

$^1$H NMR (400 MHz, DMSO-$d_6$) δ 8.32 (d, 1H, J=7.6 Hz), 8.20 (s, 1H), 8.00 (d, 1H, J=7.6 Hz), 7.94 (d, 1H, J=7.6 Hz), 7.81 (d, 1H, J=4.0 Hz), 7.65-7.60 (m, 2H), 4.09-4.04 (m, 1H), 3.90 (s, 3H), 1.18 (d, 6H, J=6.4 Hz).

Example 23: Preparation of 3-(5-(isopropylcarbamoyl)thiophen-2-yl)benzoic acid

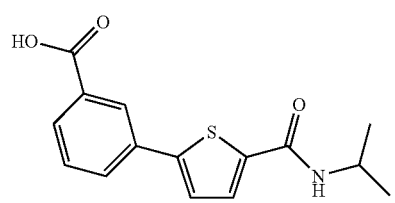 [SMILES: CC(C)NC(=O)c1ccc(-c2cccc(C(=O)O)c2)s1]

The title compound (yield: 14.30%) was obtained as a white solid in the same manner as in Example 20, except that methyl 3-(5-(isopropylcarbamoyl)thiophen-2-yl)benzoate was used instead of methyl 4-(5-(isopropylcarbamoyl)thiophen-2-yl)benzoate.

$^1$H NMR (400 MHz, DMSO-$d_6$) δ 8.33 (d, 1H, J=7.6 Hz), 8.20 (s, 1H), 7.93 (t, 2H, J=8.8 Hz), 7.82 (d, 1H, J=4.0 Hz), 7.63-7.55 (m, 2H), 4.09-4.04 (m, 1H), 1.18 (d, 6H, J=6.8 Hz).

Example 24: Preparation of N-isopropyl-5-p-tolylthiophene-2-carboxamide

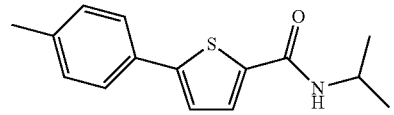 [SMILES: Cc1ccc(-c2ccc(C(=O)NC(C)C)s2)cc1]

The title compound (yield: 64.90%) was obtained as a white solid in the same manner as in Preparation Example 3, except that p-tolylboronic acid was used instead of (3,4-dimethoxyphenyl)boronic acid.

$^1$H NMR (400 MHz, DMSO-$d_6$) δ 8.24 (d, 1H, J=7.6 Hz), 7.75 (d, 1H, J=4.0 Hz), 7.59 (d, 2H, J=8.4 Hz), 7.46 (d, 1H, J=3.6 Hz), 7.24 (d, 2H, J=8.0 Hz), 4.10-4.01 (m, 1H), 2.33 (s, 3H), 1.17 (d, 6H, J=6.4 Hz).

Example 25: Preparation of 5-(4-ethylphenyl)-N-isopropylthiophene-2-carboxamide

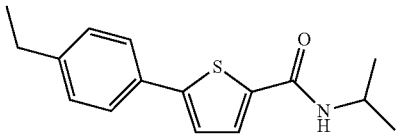 [SMILES: CCc1ccc(-c2ccc(C(=O)NC(C)C)s2)cc1]

The title compound (yield: 24.20%) was obtained as a white solid in the same manner as in Preparation Example 3, except that (4-ethylphenyl)boronic acid was used instead of (3,4-dimethoxyphenyl)boronic acid.

¹H NMR (400 MHz, DMSO-d₆) δ 8.22 (d, 1H, J=7.6 Hz), 7.74 (d, 1H, J=2.0 Hz), 7.59 (d, 2H, J=8.0 Hz), 7.45 (d, 1H, J=3.9 Hz), 7.26 (d, 2H, J=8.4 Hz), 4.08-3.99 (m, 1H), 2.63-2.58 (m, 2H), 1.19-1.14 (m, 9H).

Example 26: Preparation of N-isopropyl-5-(4-isopropylphenyl)thiophene-2-carboxamide

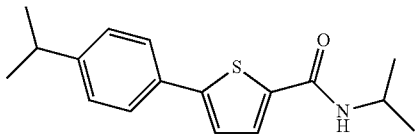 [SMILES: CC(C)NC(=O)c1ccc(-c2ccc(C(C)C)cc2)s1]

The title compound (yield: 25.30%) was obtained as a white solid in the same manner as in Preparation Example 3, except that (4-isopropylphenyl)boronic acid was used instead of (3,4-dimethoxyphenyl)boronic acid.

¹H NMR (400 MHz, DMSO-d₆) δ 8.25 (d, 1H, J=7.6 Hz), 7.77 (d, 1H, J=4.0 Hz), 7.63 (d, 2H, J=8.0 Hz), 7.48 (d, 1H, J=4.0 Hz), 7.32 (d, 2H, J=8.0 Hz), 4.11-4.03 (m, 1H), 2.98-2.87 (m, 1H), 1.21 (m, 12H).

Example 27: Preparation of 5-(3,4-difluorophenyl)-N-isopropylthiophene-2-carboxamide

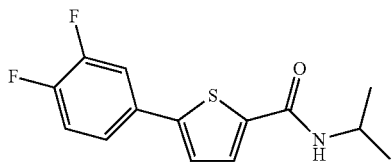 [SMILES: CC(C)NC(=O)c1ccc(-c2ccc(F)c(F)c2)s1]

The title compound (yield: 36.40%) was obtained as a white solid in the same manner as in Preparation Example 3, except that (3,4-difluorophenyl)boronic acid was used instead of (3,4-dimethoxyphenyl)boronic acid.

¹H NMR (400 MHz, DMSO-d₆) δ 8.31 (d, 1H, J=7.6 Hz), 7.78-7.83 (m, 1H), 7.79 (d, 1H, J=4.0 Hz), 7.59 (d, 1H, J=3.6 Hz), 7.55-7.48 (m, 2H), 4.11-4.03 (m, 1H), 1.19 (d, 6H, J=6.4 Hz).

Example 28: Preparation of 5-(3,5-dimethylphenyl)-N-isopropylthiophene-2-carboxamide

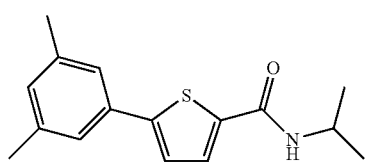 [SMILES: Cc1cc(C)cc(-c2ccc(C(=O)NC(C)C)s2)c1]

The title compound (yield: 21.90%) was obtained as a white solid in the same manner as in Preparation Example 3, except that (3,5-dimethylphenyl)boronic acid was used instead of (3,4-dimethoxyphenyl)boronic acid.

¹H NMR (400 MHz, DMSO-d₆) δ 8.23 (d, 1H, J=8.0 Hz), 7.75 (d, 1H, J=4.0 Hz), 7.47 (d, 1H, J=4.0 Hz), 7.31 (s, 2H), 6.99 (s, 1H), 4.10-4.01 (m, 1H), 2.31 (s, 6H), 1.17 (d, 6H, J=6.8 Hz).

Example 29: Preparation of 5-(4-fluorophenyl)-N-isopropylthiophene-2-carboxamide

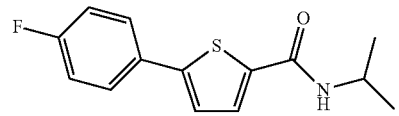 [SMILES: CC(C)NC(=O)c1ccc(-c2ccc(F)cc2)s1]

The title compound (yield: 48.20%) was obtained as a white solid in the same manner as in Preparation Example 3, except that (4-fluorophenyl)boronic acid was used instead of (3,4-dimethoxyphenyl)boronic acid.

¹H NMR (400 MHz, DMSO-d₆) δ 8.28 (d, 1H, J=8.0 Hz), 7.79-7.75 (m, 3H), 7.51 (d, 1H, J=4.0 Hz), 7.30 (t, 2H, J=8.8 Hz), 4.11-4.03 (m, 1H), 1.19 (d, 6H, J=6.8 Hz).

Example 30: Preparation of N-isopropyl-5-m-tolylthiophene-2-carboxamide

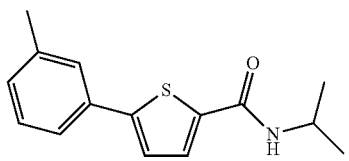 [SMILES: Cc1cccc(-c2ccc(C(=O)NC(C)C)s2)c1]

The title compound (yield: 77.10%) was obtained as a white solid in the same manner as in Preparation Example 3, except that m-tolylboronic acid was used instead of (3,4-dimethoxyphenyl)boronic acid.

¹H NMR (400 MHz, DMSO-d₆) δ 8.26 (d, 1H, J=7.6 Hz), 7.77 (d, 1H, J=3.6 Hz), 7.489-7.532 (m, 3H), 7.33 (t, 1H, J=7.6 Hz), 7.18 (d, 1H, J=7.6 Hz), 4.024-4.109 (m, 1H), 2.36 (s, 3H), 1.17 (d, 6H, J=6.4 Hz)

Example 31: Preparation of 5-(2,4-dimethylphenyl)-N-isopropylthiophene-2-carboxamide

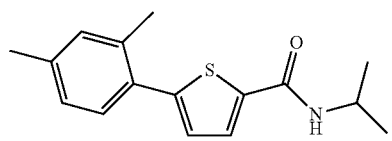 [SMILES: Cc1ccc(-c2ccc(C(=O)NC(C)C)s2)c(C)c1]

The title compound (yield: 45.90%) was obtained as a white solid in the same manner as in Preparation Example 3, except that (2,4-dimethylphenyl)boronic acid was used instead of (3,4-dimethoxyphenyl)boronic acid.

¹H NMR (400 MHz, DMSO-d₆) δ 8.24 (d, 1H, J=7.6 Hz), 7.76 (d, 1H, J=3.6 Hz), 7.29 (d, 1H, J=7.6 Hz), 7.15 (d, 2H, J=4.0 Hz), 7.08 (d, 1H, J=8.0 Hz), 4.10-4.02 (m, 1H), 2.36 (s, 3H), 2.30 (s, 3H), 1.17 (d, 6H, J=6.4 Hz).

Example 32: Preparation of 5-(4-cyanophenyl)-N-isopropylthiophene-2-carboxamide

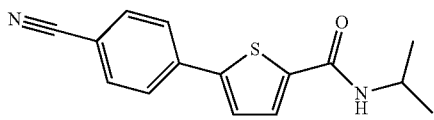 [SMILES: CC(C)NC(=O)c1ccc(-c2ccc(C#N)cc2)s1]

The title compound (yield: 39.70%) was obtained as a white solid in the same manner as in Preparation Example 3, except that 4-cyanophenylboronic acid was used instead of (3,4-dimethoxyphenyl)boronic acid.

$^1$H NMR (400 MHz, DMSO-$d_6$) δ 8.36 (d, 1H, J=8.0 Hz), 7.90 (s, 4H), 7.83 (d, 1H, J=4.0 Hz), 7.74 (d, 1H, J=4.0 Hz), 4.10-4.02 (m, 1H), 1.18 (d, 6H, J=6.8 Hz).

Example 33: Preparation of N-isopropyl-5-(4-(isopropylcarbamoyl)phenyl)thiophene-2-carboxamide

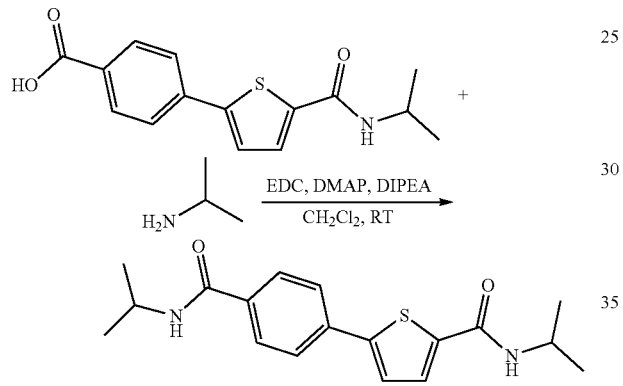

Isopropylamine (5.5 mmol), 4-(5-(isopropylcarbamoyl)thiophen-2-yl)benzoic acid (Example 20, 1.1 mmol), EDC (1.43 mmol), DMAP (1.43 mmol), and N,N-diisopropylethylamine (DIPEA; 5.5 mmol) were added to dichloromethane (20 mL), and the mixture was stirred at room temperature for 10 hours. The organic solvent was concentrated under reduced pressure and purified by flash column chromatography (n-Hx:EtOAc=5:1), and then recrystallized using dichloromethane and hexane. The product was dried by a vacuum pump to give the title compound as a white solid (yield: 4.12%).

$^1$H NMR (400 MHz, DMSO-$d_6$) δ 8.31-8.27 (m, 2H), 7.91 (d, 2H, J=8.4 Hz), 7.81-7.78 (m, 3H), 7.64 (d, 1H, J=4.0 Hz), 4.13-4.04 (m, 2H), 1.17 (d, 12H, J=6.4 Hz).

Example 34: Preparation of 5-(3,5-difluorophenyl)-N-isopropylthiophene-2-carboxamide

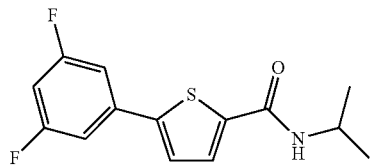 [SMILES: CC(C)NC(=O)c1ccc(-c2cc(F)cc(F)c2)s1]

The title compound (yield: 30.00%) was obtained as a white solid in the same manner as in Preparation Example 3, except that (3,5-difluorophenyl)boronic acid was used instead of (3,4-dimethoxyphenyl)boronic acid.

$^1$H NMR (400 MHz, DMSO-$d_6$) δ 8.34 (d, 1H, J=7.6 Hz), 7.80 (d, 1H, J=3.6 Hz), 7.70 (d, 1H, J=4.0 Hz), 7.48 (d, 2H, J=6.8 Hz), 7.27-7.23 (m, 1H), 4.10-4.02 (m, 1H), 1.18 (d, 6H, J=6.4 Hz).

Example 35: Preparation of 5-(4-ethoxyphenyl)-N-isopropylthiophene-2-carboxamide

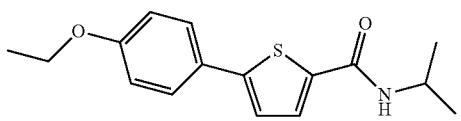 [SMILES: CCOc1ccc(-c2ccc(C(=O)NC(C)C)s2)cc1]

The title compound was obtained as a white solid in the same manner as in Preparation Example 3, except that (4-ethoxyphenyl)boronic acid was used instead of (3,4-dimethoxyphenyl)boronic acid.

$^1$H NMR (400 MHz, DMSO-$d_6$) δ 8.20 (d, 1H, J=10.4 Hz), 7.74 (d, 1H, J=5.2 Hz), 7.62 (d, 2H, J=12.0 Hz), 7.39 (d, 1H, J=5.2 Hz), 7.00 (d, 2H, J=22.0 Hz), 4.10-4.02 (m, 3H), 1.35 (t, 3H, J=9.2 Hz), 1.17 (d, 6H, J=8.8 Hz)

Example 36: Preparation of 5-(4-(ethylcarbamoyl)phenyl)-N-isopropylthiophene-2-carboxamide

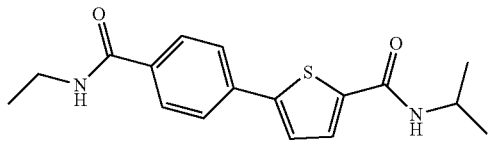 [SMILES: CCNC(=O)c1ccc(-c2ccc(C(=O)NC(C)C)s2)cc1]

The title compound (yield: 11.5%) was obtained as a white solid in the same manner as in Example 33, except that ethylamine hydrochloride was used instead of isopropylamine.

$^1$H NMR (300 MHz, DMSO-$d_6$) δ 8.49 (t, 1H, J=5.45 Hz), 8.27 (d, 1H, J=7.71 Hz), 7.89-7.86 (m, 2H), 7.78-7.74 (m, 3H), 7.61 (d, 1H, J=3.94 Hz), 4.03 (dq, 1H J=6.50, 13.09 Hz), 3.32-3.23 (m, 2H), 1.15 (d, 6H, J=6.60 Hz), 1.11 (t, 3H, J=7.21 Hz)

Example 37: Preparation of N-isopropyl-5-(4-(phenylcarbamoyl)phenyl)thiophene-2-carboxamide

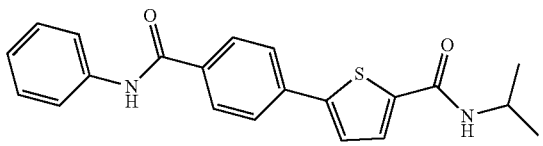 [SMILES: CC(C)NC(=O)c1ccc(-c2ccc(C(=O)Nc3ccccc3)cc2)s1]

The title compound (yield: 38.7%) was obtained as an ocher solid in the same manner as in Example 33, except that aniline was used instead of isopropylamine.

$^1$H NMR (300 MHz, DMSO-$d_6$) δ 10.30 (s, 1H), 8.33 (d, 1H, J=7.71 Hz), 8.04 (d, 2H, J=8.52 Hz), 7.89-7.79 (m, 5H), 7.69 (d, 1H, J=3.95 Hz), 7.40-7.35 (m, 2H), 7.15-7.10 (m, 1H), 4.14-4.04 (m, 1H), 1.19 (d, 6H, J=6.61 Hz)

In the following Examples 38 to 91, respective compounds were prepared in the same manner as in Preparation Example 3, except that the starting materials were changed in compliance with the structures of the respective compounds to be prepared.

Example 38: Preparation of 5-(2,4-dimethylphenyl)-N-isopropylfuran-2-carboxamide

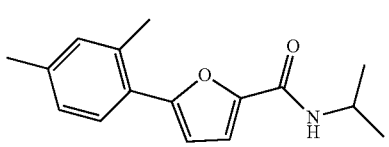 [SMILES: Cc1ccc(-c2ccc(C(=O)NC(C)C)o2)c(C)c1]

¹H NMR (400 MHz, DMSO-d₆) δ 8.12 (d, 1H, J=10.4 Hz), 7.79 (t, 1H, J=5.6 Hz), 7.18-7.12 (m, 3H), 6.76 (d, 1H, J=4.8 Hz), 4.16-4.04 (m, 1H), 2.44 (s, 3H), 2.31 (s, 3H), 1.18 (d, 6H, J=8.8 Hz)

Example 39: Preparation of 5-(3,4-difluorophenyl)-N-isopropylfuran-2-carboxamide

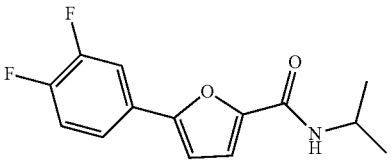 [SMILES: CC(C)NC(=O)c1ccc(-c2ccc(F)c(F)c2)o1]

¹H NMR (400 MHz, DMSO-d₆) δ 8.25 (d, 1H, J=10.4 Hz), 8.12-8.04 (m, 1H), 7.81-7.76 (m, 1H), 7.60-7.51 (m, 1H), 7.16-7.13 (m, 2H), 4.17-4.06 (m, 1H), 1.12 (d, 6H, J=8.8 Hz)

Example 40: Preparation of 5-(4-ethylphenyl)-N-isopropylfuran-2-carboxamide

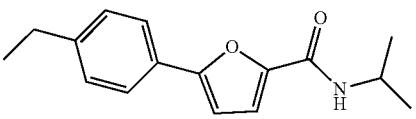 [SMILES: CCc1ccc(-c2ccc(C(=O)NC(C)C)o2)cc1]

¹H NMR (300 MHz, DMSO-d₆) δ 8.16 (d, J=7.9 Hz, 1H), 7.84-7.83 (m, 1H), 7.82-7.80 (m, 1H), 7.31 (d, J=8.6 Hz, 2H), 7.13 (d, J=3.6 Hz, 1H), 7.00 (d, J=3.5 Hz, 1H), 4.14-4.07 (m, 1H), 2.64 (q, J=7.5 Hz, 2H), 1.23-1.18 (m, 9H)

Example 41: Preparation of N-isopropyl-5-m-tolylfuran-2-carboxamide

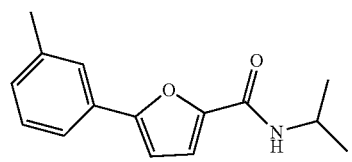 [SMILES: Cc1cccc(-c2ccc(C(=O)NC(C)C)o2)c1]

¹H NMR (300 MHz, DMSO-d₆) δ 8.17 (d, 1H, J=8.1 Hz), 7.73-7.70 (m, 2H), 7.35 (t, 1H, J=7.9 Hz), 7.18 (d, 1H, J=7.5 Hz), 7.15 (d, 1H, J=3.6 Hz), 7.04 (d, 1H, J=3.3 Hz), 4.17-4.05 (m, 1H), 2.38 (s, 3H), 1.19 (d, 6H, J=6.6 Hz)

Example 42: Preparation of 5-(4-ethoxyphenyl)-N-isopropylfuran-2-carboxamide

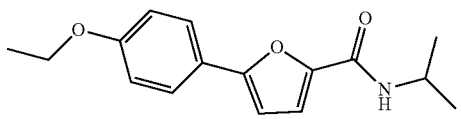 [SMILES: CCOc1ccc(-c2ccc(C(=O)NC(C)C)o2)cc1]

¹H NMR (300 MHz, DMSO-d₆) δ 8.13 (d, 1H, J=13.5 Hz), 7.86-7.81 (m, 2H), 7.11 (d, 1H, J=3.6 Hz), 7.04-6.99 (m, 2H), 6.90 (d, 2H, J=3.6 Hz), 4.14-4.05 (m, 3H), 1.35 (t, 3H, J=3.6 Hz), 1.19 (d, 6H, J=6.6 Hz)

Example 43: Preparation of N-isopropyl-5-p-tolylfuran-2-carboxamide

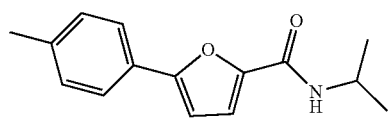 [SMILES: Cc1ccc(-c2ccc(C(=O)NC(C)C)o2)cc1]

¹H NMR (300 MHz, DMSO-d₆) δ 8.16 (d, 1H, J=7.8 Hz), 7.80 (d, 2H, J=5.4 Hz), 7.28 (d, 2H, J=8.1 Hz), 7.13 (d, 1H, J=3.6 Hz), 7.00 (d, 1H, J=3.6 Hz), 4.16-4.05 (m, 1H), 2.34 (s, 1H), 1.19 (d, 6H, J=6.6 Hz)

Example 44: Preparation of N-isopropyl-5-phenylfuran-2-carboxamide

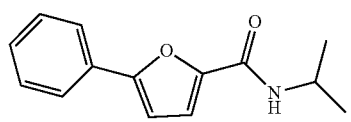 [SMILES: CC(C)NC(=O)c1ccc(-c2ccccc2)o1]

¹H NMR (300 MHz, DMSO-d₆) δ 8.20 (d, 1H, J=8.1 Hz), 7.94-7.91 (m, 2H), 7.50-7.45 (m, 2H), 7.40-7.35 (m, 1H), 7.16-7.15 (m, 1H), 7.09-7.07 (m, 1H), 4.17-4.06 (m, 1H), 1.20 (d, 6H, J=6.6 Hz)

Example 45: Preparation of N-isopropyl-5-(4-isopropylphenyl)furan-2-carboxamide

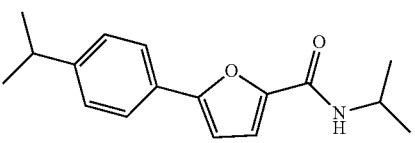 [SMILES: CC(C)NC(=O)c1ccc(-c2ccc(C(C)C)cc2)o1]

¹H NMR (300 MHz, DMSO-d₆) δ 8.16 (d, 1H, J=8.1 Hz), 7.82 (d, 2H, J=8.4 Hz), 7.34 (d, 2H, J=8.1 Hz), 7.14 (d, 1H,

J=3.6 Hz), 6.99 (d, 1H, J=3.6 Hz), 4.16-4.05 (m, 1H), 3.00-2.86 (m, 1H), 1.23 (d, 6H, J=6.9 Hz), 1.19 (d, 6H, J=6.6 Hz)

Example 46: Preparation of 5-(4-cyanophenyl)-N-isopropylfuran-2-carboxamide

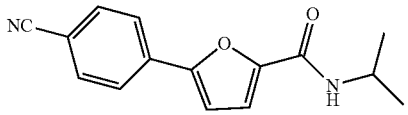 [SMILES: CC(C)NC(=O)c1ccc(-c2ccc(C#N)cc2)o1]

$^1$H NMR (300 MHz, DMSO-d$_6$) δ 8.34 (d, 1H, J=7.8 Hz), 8.13 (d, 2H, J=8.7 Hz), 7.95 (d, 2H, J=8.7 Hz), 7.34 (d, 1H, J=3.6 Hz), 7.20 (d, 1H, J=3.6 Hz), 4.18-4.06 (m, 1H), 1.20 (d, 6H, J=6.6 Hz)

Example 47: Preparation of 5-(3,5-dimethylphenyl)-N-phenylfuran-2-carboxamide

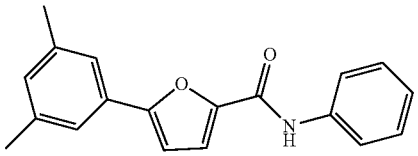

$^1$H NMR (300 MHz, DMSO-d$_6$) δ 10.14 (s, 1H), 7.79-7.75 (m, 2H), 7.59-7.58 (m, 2H), 7.41-7.35 (m, 3H), 7.15-7.10 (m, 2H), 7.04-7.03 (m, 1H), 2.35 (d, J=0.5 Hz, 6H)

Example 48: Preparation of 5-(3,5-dimethylphenyl)-N-phenylthiophene-2-carboxamide

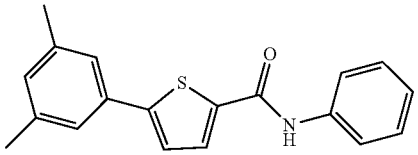 [SMILES: Cc1cc(C)cc(-c2ccc(C(=O)Nc3ccccc3)o2)c1]

$^1$H NMR (300 MHz, DMSO-d$_6$) δ 10.24 (s, 1H), 8.03 (d, 2H, J=4.2 Hz), 7.75 (d, 2H, J=7.5 Hz), 7.60 (d, 1H, J=3.9 Hz), 7.37 (t, 4H, J=7.8 Hz), 7.12 (t, 1H, J=7.3 Hz), 7.036 (s, 1H), 2.33 (s, 6H)

Example 49: Preparation of N-phenyl-5-(pyridin-3-yl)thiophene-2-carboxamide

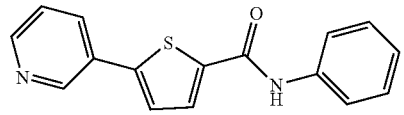 [SMILES: O=C(Nc1ccccc1)c1ccc(-c2cccnc2)s1]

$^1$H NMR (300 MHz, DMSO-d$_6$) δ 10.32 (s, 1H), 7.73 (dd, 1H, J=0.6 Hz), 7.73 (dd, 1H, J=1.5 Hz), 8.18-8.08 (m, 2H), 7.76 (t, 3H, J=6.0 Hz), 7.53-7.49 (m, 1H), 7.38 (t, 2H, J=7.9 Hz), 7.13 (t, 1H, J=7.4 Hz)

Example 50: Preparation of N-ethyl-5-(pyridin-3-yl)thiophene-2-carboxamide

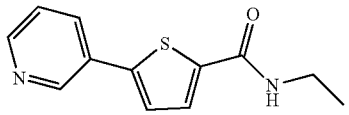 [SMILES: CCNC(=O)c1ccc(-c2cccnc2)s1]

$^1$H NMR (300 MHz, DMSO-d$_6$) δ 8.95 (dd, 1H, J=0.6 Hz), 8.57-8.54 (m, 2H), 8.12-8.08 (m, 1H), 7.77 (d, 1H, J=3.9 Hz), 7.66 (d, 1H, J=3.9 Hz), 7.50-7.45 (m, 1H), 3.31-3.24 (m, 2H), 1.14 (t, 3H, J=7.2 Hz)

Example 51: Preparation of 5-(3,4-difluorophenyl)-N-phenylfuran-2-carboxamide

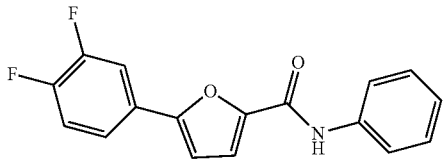 [SMILES: O=C(Nc1ccccc1)c1ccc(-c2ccc(F)c(F)c2)o1]

$^1$H NMR (300 MHz, DMSO-d$_6$) δ 10.20 (s, 1H), 8.15 (ddd, J=11.8, 8.0, 2.1 Hz, 1H), 7.88-7.84 (m, 1H), 7.75 (dd, J=8.6, 1.1 Hz, 2H), 7.60 (dt, J=10.5, 8.6 Hz, 1H), 7.41-7.36 (m, 3H), 7.26 (d, J=3.6 Hz, 1H), 7.17-7.12 (m, 1H)

Example 52: Preparation of N-phenyl-5-p-tolylfuran-2-carboxamide

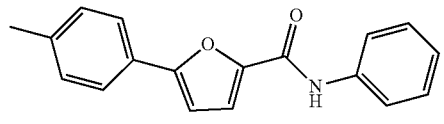 [SMILES: Cc1ccc(-c2ccc(C(=O)Nc3ccccc3)o2)cc1]

$^1$H NMR (300 MHz, DMSO-d$_6$) δ 10.14 (s, 1H), 7.87 (d, J=8.2 Hz, 2H), 7.78-7.75 (m, 2H), 7.40-7.30 (m, 5H), 7.15-7.10 (m, 2H), 2.36 (s, 3H)

Example 53: Preparation of N-phenyl-5-(pyridin-3-yl)furan-2-carboxamide

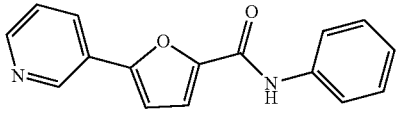 [SMILES: O=C(Nc1ccccc1)c1ccc(-c2cccnc2)o1]

$^1$H NMR (300 MHz, DMSO-d$_6$) δ 10.22 (s, 1H), 9.25 (dd, J=2.3, 0.8 Hz, 1H), 8.59 (dd, J=4.8, 1.6 Hz, 1H), 8.35 (ddd, J=8.0, 2.3, 1.6 Hz, 1H), 7.78-7.75 (m, 2H), 7.54 (ddd, J=8.0, 4.8, 0.9 Hz, 1H), 7.44 (d, J=3.7 Hz, 1H), 7.42-7.36 (m, 2H), 7.34 (d, J=3.6 Hz, 1H), 7.17-7.11 (m, 1H)

Example 54: Preparation of 5-(4-hydroxy-3-methoxyphenyl)-N-isopropylfuran-2-carboxamide

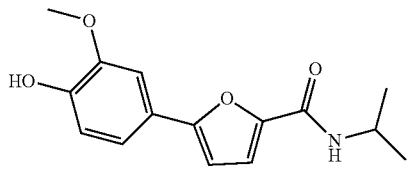 [SMILES: COc1cc(-c2ccc(C(=O)NC(C)C)o2)ccc1O]

$^1$H NMR (300 MHz, DMSO-d$_6$) δ 9.37 (s, 1H), 8.09 (d, J=8.1 Hz, 1H), 7.39-7.36 (m, 2H), 7.12 (d, J=3.6 Hz, 1H), 6.90-6.84 (m, 2H), 4.16-4.04 (m, 1H), 3.86 (s, 3H), 1.19 (d, J=6.6 Hz, 6H)

Example 55: Preparation of N,5-di(pyridin-3-yl)thiophene-2-carboxamide

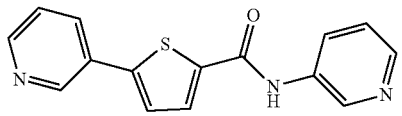 [SMILES: O=C(Nc1cccnc1)c1ccc(-c2cccnc2)s1]

$^1$H NMR (300 MHz, DMSO-d$_6$) δ 10.56 (s, 1H), 9.00 (d, 1H, J=1.8 Hz), 8.92 (d, 1H, J=2.1 Hz), 8.58 (dd, 1H, J=1.5 Hz), 8.33 (dd, 1H, J=1.3 Hz), 8.19-8.12 (m, 3H), 7.77 (d, 1H, J=3.9 Hz), 7.52-7.48 (m, 1H), 7.41 (q, 1H, J=4.8 Hz)

Example 56: Preparation of 5-(4-hydroxy-3-methoxyphenyl)-N-phenylfuran-2-carboxamide

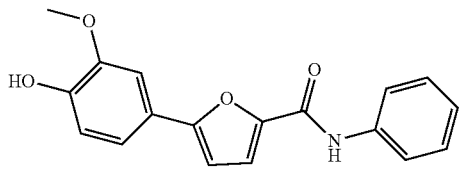 [SMILES: COc1cc(-c2ccc(C(=O)Nc3ccccc3)o2)ccc1O]

$^1$H NMR (300 MHz, DMSO-d$_6$) δ 10.08 (s, 1H), 9.43 (s, 1H), 7.76 (dd, J=8.7, 1.1 Hz, 2H), 7.47-7.34 (m, 5H), 7.14-7.09 (m, 1H), 7.00 (d, J=3.6 Hz, 1H), 6.88 (d, J=8.2 Hz, 1H), 3.88 (s, 3H)

Example 57: Preparation of 5-(3,4-dimethoxyphenyl)-N-(pyridin-3-yl)furan-2-carboxamide

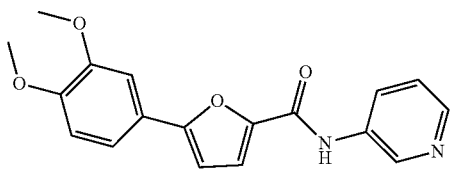 [SMILES: COc1ccc(-c2ccc(C(=O)Nc3cccnc3)o2)cc1OC]

$^1$H NMR (300 MHz, DMSO-d$_6$) δ 10.33 (s, 1H), 8.94 (d, 1H, J=2.1 Hz), 8.34-8.32 (m, 1H), 8.18-8.15 (m, 1H), 7.56-7.43 (m, 4H), 7.11-7.07 (m, 2H), 3.85 (d, 6H, J=15.0 Hz)

Example 58: Preparation of N,5-di(pyridin-3-yl)furan-2-carboxamide

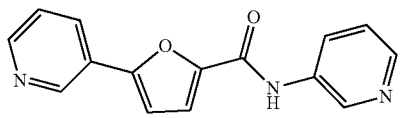

$^1$H NMR (300 MHz, DMSO-d$_6$) δ 10.43 (s, 1H), 9.25 (t, 1H, J=1.2 Hz), 8.94 (d, 1H, J=2.1 Hz), 8.62-8.59 (m, 1H), 8.37-8.34 (m, 2H), 8.20-8.16 (m, 1H), 7.58-7.36 (m, 4H)

Example 59: Preparation of 5-(4-hydroxy-3-methoxyphenyl)-N-(pyridin-3-yl)furan-2-carboxamide

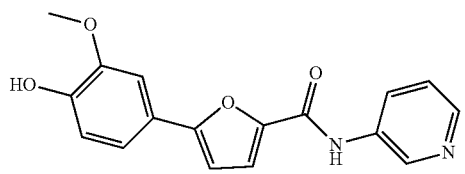

$^1$H NMR (300 MHz, DMSO-d$_6$) δ 10.29 (s, 1H), 9.46 (s, 1H), 8.94 (d, 1H, J=2.4 Hz), 8.34-8.32 (m, 1H), 8.16-8.15 (m, 1H), 7.46-7.41 (m, 4H), 7.02 (d, 1H, J=3.6 Hz), 6.89 (d, 1H, J=8.1 Hz), 3.89 (s, 3H)

Example 60: Preparation of 5-(4-hydroxy-3-methoxyphenyl)-N-(pyridin-3-yl)thiophene-2-carboxamide

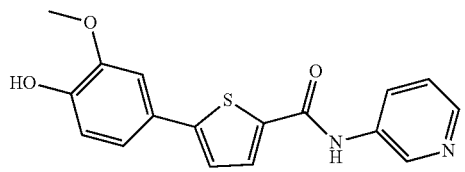 [SMILES: COc1cc(-c2ccc(C(=O)Nc3cccnc3)o2)ccc1O]

$^1$H NMR (300 MHz, DMSO-d$_6$) δ 10.38 (s, 1H), 9.44 (s, 1H), 8.90 (d, J=2.3 Hz, 1H), 8.31 (dd, J=4.7, 1.4 Hz, 1H), 8.17-8.14 (m, 1H), 8.00 (d, J=4.0 Hz, 1H), 7.51 (d, J=4.0 Hz, 1H), 7.40 (dd, J=8.3, 4.7 Hz, 1H), 7.27 (d, J=2.1 Hz, 1H), 7.17 (dd, J=8.2, 2.1 Hz, 1H), 6.85 (d, J=8.2 Hz, 1H), 3.87 (s, 3H)

Example 61: Preparation of 5-(2-aminophenyl)-N-isopropylfuran-2-carboxamide

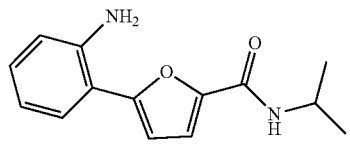 [SMILES: CC(C)NC(=O)c1ccc(-c2ccccc2N)o1]

$^1$H NMR (300 MHz, DMSO-d$_6$) δ 8.15 (d, J=8.0 Hz, 1H), 7.62 (dd, J=7.9, 1.5 Hz, 1H), 7.18 (d, J=3.6 Hz, 1H), 7.09

(ddd, J=8.5, 7.2, 1.6 Hz, 1H), 6.85-6.81 (m, 2H), 6.66 (ddd, J=8.2, 7.2, 1.2 Hz, 1H), 5.46 (s, 2H), 4.21-3.99 (m, 1H), 1.18 (d, J=6.6 Hz, 6H)

Example 62: Preparation of N-isopropyl-5-(quinolin-3-yl)furan-2-carboxamide

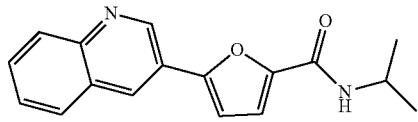 [SMILES: CC(C)NC(=O)c1ccc(-c2cnc3ccccc3c2)o1]

$^1$H NMR (300 MHz, DMSO-d$_6$) δ 9.49 (d, J=2.2 Hz, 1H), 8.81 (d, J=2.0 Hz, 1H), 8.33 (d, J=8.0 Hz, 1H), 8.08-8.05 (m, 2H), 7.79 (ddd, J=8.4, 6.9, 1.5 Hz, 1H), 7.68 (ddd, J=1.13, 6.99, 8.11 Hz, 1H), 7.39 (d, J=3.6 Hz, 1H), 7.26 (d, J=3.6 Hz, 1H), 4.21-4.10 (m, 1H), 1.23 (d, J=6.6 Hz, 6H)

Example 63: Preparation of N-isopropyl-5-(2-oxoindolin-5-yl)furan-2-carboxamide

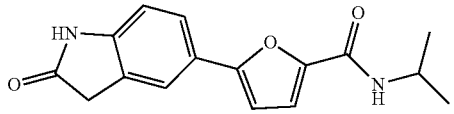 [SMILES: CC(C)NC(=O)c1ccc(-c2ccc3c(c2)CC(=O)N3)o1]

$^1$H NMR (300 MHz, DMSO-d$_6$) δ 10.55 (s, 1H), 8.13 (d, J=8.1 Hz, 1H), 7.78-7.74 (m, 2H), 7.11 (d, J=3.6 Hz, 1H), 6.91-6.87 (m, 2H), 4.19-4.03 (m, 1H), 3.56 (s, 2H), 1.19 (d, J=6.6 Hz, 6H)

Example 64: Preparation of 5-(1H-indol-5-yl)-N-isopropylfuran-2-carboxamide

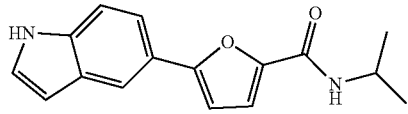 [SMILES: CC(C)NC(=O)c1ccc(-c2ccc3[nH]ccc3c2)o1]

$^1$H NMR (300 MHz, DMSO-d$_6$) δ 11.26 (s, 1H), 8.15-8.12 (m, 2H), 7.64 (dd, J=8.5, 1.6 Hz, 1H), 7.47-7.40 (m, 2H), 7.13 (d, J=3.5 Hz, 1H), 6.90 (d, J=3.5 Hz, 1H), 6.52-6.51 (m, 1H), 4.17-4.10 (m, 1H), 1.21 (d, J=6.6 Hz, 6H)

Example 65: Preparation of N-isopropyl-5-(isoquinolin-4-yl)furan-2-carboxamide

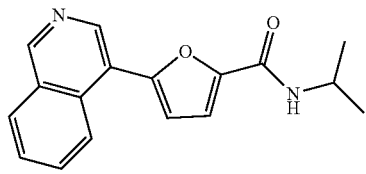 [SMILES: CC(C)NC(=O)c1ccc(-c2cncc3ccccc23)o1]

$^1$H NMR (300 MHz, DMSO-d$_6$) δ 9.37 (s, 1H), 9.01 (s, 1H), 8.43 (d, J=8.5 Hz, 1H), 8.33-8.24 (m, 2H), 7.96-7.90 (m, 1H), 7.80 (t, J=7.2 Hz, 1H), 7.34 (d, J=3.6 Hz, 1H), 7.24 (d, J=3.6 Hz, 1H), 4.22-4.06 (m, 1H), 1.21 (d, J=6.6 Hz, 6H)

Example 66: Preparation of N-isopropyl-5-(pyridin-3-yl)furan-2-carboxamide

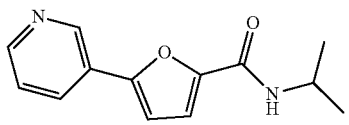 [SMILES: CC(C)NC(=O)c1ccc(-c2cccnc2)o1]

$^1$H NMR (300 MHz, DMSO-d$_6$) δ 9.20-9.19 (m, 1H), 8.57-8.55 (m, 1H), 8.31-8.27 (m, 2H), 7.53-7.48 (m, 1H), 7.24-7.18 (m, 2H), 4.20-4.04 (m, 1H), 1.20 (d, 6H, J=6.6 Hz)

Example 67: Preparation of isopropyl 5-(pyridin-3-yl)furan-2-carboxylate

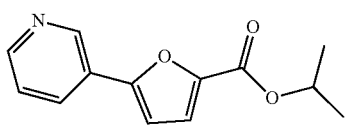 [SMILES: CC(C)OC(=O)c1ccc(-c2cccnc2)o1]

$^1$H NMR (300 MHz, DMSO-d$_6$) δ 9.05 (s, 1H), 8.62-8.61 (m, 1H), 8.18-8.17 (m, 1H), 7.55-7.33 (m, 3H), 5.20-5.10 (m, 1H), 1.34 (d, 6H, J=6.3 Hz)

Example 68: Preparation of ethyl 5-(pyridin-3-yl)furan-2-carboxylate

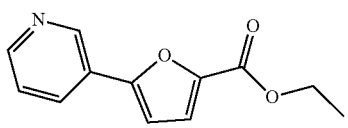

$^1$H NMR (300 MHz, DMSO) δ 9.05 (dd, J=2.3, 0.8 Hz, 1H), 8.60 (dd, J=4.8, 1.6 Hz, 1H), 8.20-8.16 (m, 1H), 7.55-7.51 (m, 1H), 7.45 (d, J=3.7 Hz, 1H), 7.34 (d, J=3.7 Hz, 1H), 4.33 (q, J=7.1 Hz, 2H), 1.32 (t, J=7.1 Hz, 3H)

Example 69: Preparation of phenyl 5-(pyridin-3-yl)furan-2-carboxylate

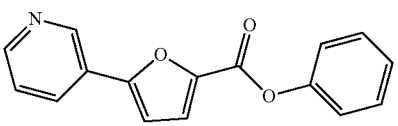 [SMILES: O=C(Oc1ccccc1)c1ccc(-c2cccnc2)o1]

$^1$H NMR (300 MHz, CDCl$_3$) δ 9.06 (s, 1H), 8.62-8.61 (m, 1H), 8.16-8.12 (m, 1H), 7.49-7.37 (m, 4H), 7.31-7.28 (m, 1H), 7.25-7.23 (m, 2H), 6.93 (d, 1H, J=3.9 Hz)

Example 70: Preparation of pyridin-3-yl 5-(pyridin-3-yl)furan-2-carboxylate

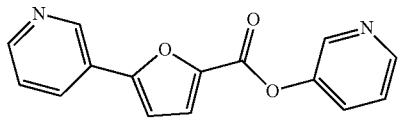 [SMILES: O=C(Oc1cccnc1)c1ccc(-c2cccnc2)o1]

¹H NMR (300 MHz, CDCl₃) δ 9.07-9.06 (m, 1H), 8.60-8.54 (m, 3H), 8.16-8.13 (m, 1H), 7.67-7.63 (m, 1H), 7.53 (d, J=3.7 Hz, 1H), 7.43-7.38 (m, 2H), 6.95 (d, J=3.7 Hz, 1H)

Example 71: Preparation of ethyl 5-(pyridin-3-yl)thiophene-2-carboxylate

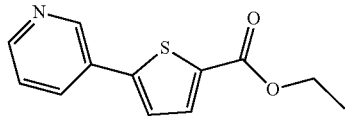 [SMILES: CCOC(=O)c1ccc(-c2cccnc2)s1]

¹H NMR (300 MHz, DMSO-d₆) δ 9.01-9.00 (m, 1H), 8.61-8.59 (m, 1H), 8.19-8.15 (m, 1H), 7.85-7.84 (m, 1H), 7.77-7.74 (m, 1H), 7.52-7.48 (m, 1H), 4.32 (q, 2H, J=7.2 Hz), 1.32 (t, 3H, J=7.2 Hz)

Example 72: Preparation of isopropyl 5-(pyridin-3-yl)thiophene-2-carboxylate

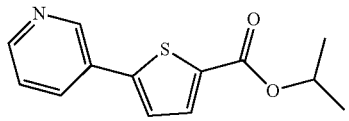 [SMILES: CC(C)OC(=O)c1ccc(-c2cccnc2)s1]

¹H NMR (300 MHz, DMSO-d₆) δ 9.00-8.99 (m, 1H), 8.60-8.58 (m, 1H), 8.19-8.15 (m, 1H), 7.83-7.81 (m, 1H), 7.74-7.73 (m, 1H), 7.52-7.47 (m, 1H), 1.32 (d, 6H, J=6.3 Hz)

Example 73: Preparation of phenyl 5-(pyridin-3-yl)thiophene-2-carboxylate

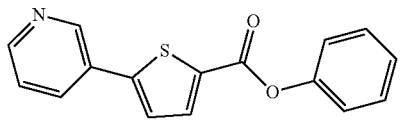 [SMILES: O=C(Oc1ccccc1)c1ccc(-c2cccnc2)s1]

¹H NMR (300 MHz, CDCl₃) δ 8.96-8.95 (m, 1H), 8.63-8.61 (m, 1H), 7.99-7.92 (m, 2H), 7.47-7.39 (m, 4H), 7.31-7.26 (m, 1H), 7.25-7.22 (m, 2H)

Example 74: Preparation of pyridin-3-yl 5-(pyridin-3-yl)thiophene-2-carboxylate

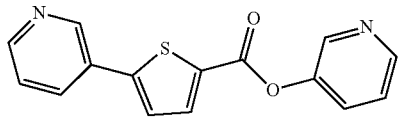 [SMILES: O=C(Oc1cccnc1)c1ccc(-c2cccnc2)s1]

¹H NMR (300 MHz, DMSO-d₆) δ 9.08-9.07 (m, 1H), 8.65-8.61 (m, 2H), 8.56-8.54 (m, 1H), 8.26-8.22 (m, 1H), 8.13-8.12 (m, 1H), 7.88-7.83 (m, 2H), 7.58-7.51 (m, 2H)

Example 75: Preparation of 5-(3-hydroxyphenyl)-N-isopropylfuran-2-carboxamide

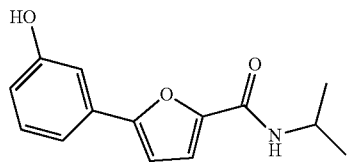 [SMILES: CC(C)NC(=O)c1ccc(-c2cccc(O)c2)o1]

¹H NMR (300 MHz, DMSO-d₆) δ 9.67 (s, 1H), 8.22 (d, 1H, J=8.1 Hz), 7.34-7.22 (m, 3H), 7.14-7.13 (m, 1H), 6.99-6.98 (m, 1H), 6.79-6.76 (m, 1H), 4.16-4.04 (m, 1H), 1.18 (d, 6H, J=6.6 Hz)

Example 76: Preparation of 5-(3,4-dimethoxyphenyl)-N-isopropylfuran-2-carboxamide

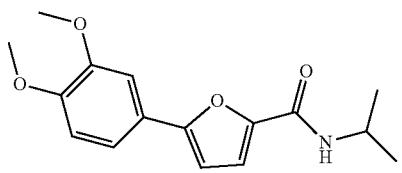 [SMILES: COc1ccc(-c2ccc(C(=O)NC(C)C)o2)cc1OC]

¹H NMR (300 MHz, DMSO-d₆) δ 8.11 (d, 1H, J=7.8 Hz), 7.48 (q, 1H, J=2.1 Hz), 7.39 (d, 1H, J=2.1 Hz), 7.13 (d, 1H, J=3.6 Hz), 7.04 (d, 1H, J=8.4 Hz), 6.97 (d, 1H, J=3.6 Hz), 4.13-4.06 (m, 1H), 3.83 (d, 6H, J=12.6 Hz), 1.19 (d, 6H, J=6.6 Hz)

Example 77: Preparation of ethyl 5-(3,4-dimethoxyphenyl)furan-2-carboxylate

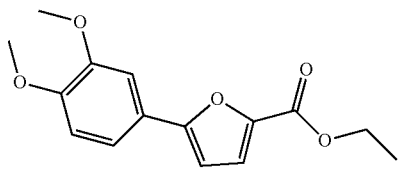 [SMILES: CCOC(=O)c1ccc(-c2ccc(OC)c(OC)c2)o1]

The title compound (yield: 48.3%) was obtained as an ocher oil in the same manner as in Preparation Example 3, except that Intermediate 4 was used instead of 5-bromo-N-isopropylthiophene-2-carboxamide.

¹H NMR (300 MHz, DMSO-d₆) δ 7.40-7.36 (m, 2H), 7.34 (d, 1H, J=2.1 Hz), 7.09-7.05 (m, 2H), 4.31 (q, 2H, J=7.2 Hz), 3.83 (d, 6H, J=10.5 Hz), 1.31 (t, 3H, J=10.5 Hz)

Example 78: Preparation of 5-(3,5-difluorophenyl)-N-isopropylfuran-2-carboxamide

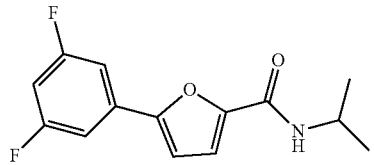 [SMILES: CC(C)NC(=O)c1ccc(-c2cc(F)cc(F)c2)o1]

¹H NMR (300 MHz, DMSO-d₆) δ 8.30 (d, 1H, J=7.8 Hz), 7.79-7.70 (m, 2H), 7.29-7.16 (m, 3H), 4.18-4.07 (m, 1H), 1.20 (d, 6H, J=6.9 Hz)

Example 79: Preparation of ethyl 5-(2-aminophenyl)furan-2-carboxylate

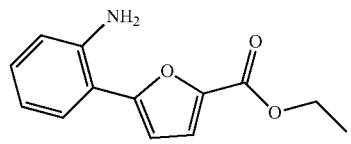 [SMILES: CCOC(=O)c1ccc(-c2ccccc2N)o1]

¹H NMR (300 MHz, DMSO-d₆) δ 7.51 (q, 1H, J=0 Hz), 7.40 (d, 1H, J=6 Hz), 7.14-7.09 (m, 1H), 6.5 (d, 1H, J=6 Hz), 6.83 (q, 1H, J=0 Hz), 6.69-6.64 (m, 1H), 5.54 (s, 2H), 4.31 (q, 2H, J=6 Hz), 1.31 (t, 3H, J=7.5 Hz)

Example 80: Preparation of ethyl 5-(isoquinolin-4-yl)furan-2-carboxylate

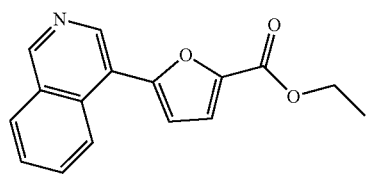 [SMILES: CCOC(=O)c1ccc(-c2cncc3ccccc23)o1]

¹H NMR (300 MHz, DMSO-d₆) δ 9.40 (d, 1H, J=0 Hz), 8.87 (s, 1H), 8.44 (q, 1H, J=0 Hz), 8.27 (d, 1H, J=9 Hz), 7.97-7.92 (m, 1H), 7.83-7.78 (m, 1H), 7.54 (d, 1H, J=3 Hz), 7.32 (d, 1H, J=3 Hz), 4.36 (q, 2H, J=6 Hz), 1.34 (t, 3H, J=7.5 Hz)

Example 81: Preparation of ethyl 5-(4-(methoxycarbonyl)phenyl)furan-2-carboxylate

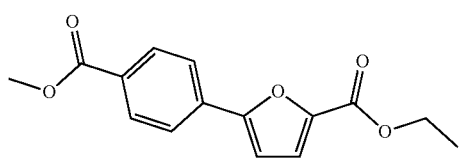 [SMILES: CCOC(=O)c1ccc(-c2ccc(C(=O)OC)cc2)o1]

¹H NMR (300 MHz, DMSO-d₆) δ 8.08-7.95 (m, 4H), 7.45 (d, 1H, J=6 Hz), 7.37 (d, 1H, J=3 Hz), 4.34 (q, 2H, J=6 Hz), 3.89 (d, 3H, J=3 Hz), 1.33 (t, 3H, J=7.5 Hz)

Example 82: Preparation of ethyl 5-(3,5-difluorophenyl)furan-2-carboxylate

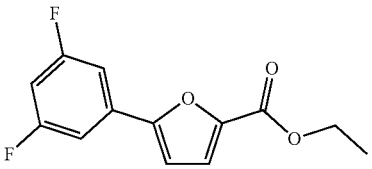 [SMILES: CCOC(=O)c1ccc(-c2cc(F)cc(F)c2)o1]

¹H NMR (300 MHz, DMSO-d₆) δ 7.55-7.52 (m, 2H), 7.45 (d, 1H, J=3 Hz), 7.38 (d, 1H, J=3 Hz), 7.35-7.28 (m, 1H), 4.33 (q, 2H, J=6 Hz), 1.33 (t, 3H, J=7.5 Hz)

Example 83: Preparation of 5-(3,5-dimethylphenyl)-N-(pyridin-3-yl)furan-2-carboxamide

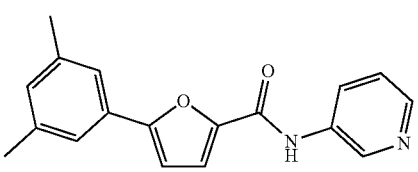 [SMILES: Cc1cc(C)cc(-c2ccc(C(=O)Nc3cccnc3)o2)c1]

¹H NMR (300 MHz, DMSO-d₆) δ 10.35 (s, 1H), 8.95 (d, 1H, J=3 Hz), 8.34 (q, 1H, J=0 Hz), 8.19-8.15 (m, 1H), 7.59 (t, 2H, J=0 Hz), 7.45-7.40 (m, 2H), 7.15 (d, 1H, J=3 Hz), 7.05 (s, 1H), 2.36 (d, 6H, J=0 Hz)

Example 84: Preparation of 5-(2,4-dimethylphenyl)-N-(pyridin-3-yl)furan-2-carboxamide

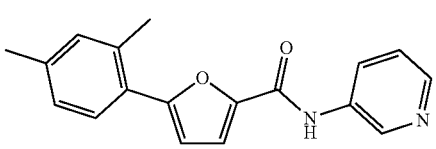 [SMILES: Cc1ccc(-c2ccc(C(=O)Nc3cccnc3)o2)c(C)c1]

¹H NMR (300 MHz, DMSO-d₆) δ 10.34 (s, 1H), 8.93 (d, 1H, J=0 Hz), 8.33 (q, 1H, J=3 Hz), 8.19-8.15 (m, 1H), 7.84 (d, 1H, J=9 Hz), 7.48 (d, 1H, J=6 Hz), 7.43-7.39 (m, 1H), 7.18-7.17 (m, 2H), 6.90 (d, 1H, J=3 Hz), 2.48 (s, 3H), 2.33 (s, 3H)

Example 85: Preparation of 5-(3,5-dimethylphenyl)-N-isopropylfuran-2-carboxamide

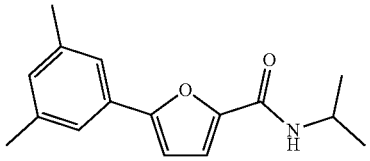 [SMILES: Cc1cc(C)cc(-c2ccc(C(=O)NC(C)C)o2)c1]

¹H NMR (300 MHz, DMSO-d₆) δ 8.15 (d, J=8.1 Hz, 1H), 7.53-7.49 (m, 2H), 7.14 (d, J=3.6 Hz, 1H), 7.02-7.00 (m, 2H), 4.20-3.99 (m, 1H), 2.33 (d, J=0.5 Hz, 6H), 1.20 (d, J=6.6 Hz, 6H)

Example 86: Preparation of ethyl 5-(3,5-dimethylphenyl)furan-2-carboxylate

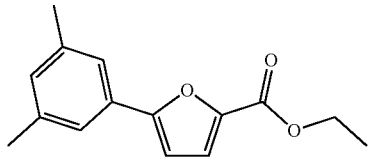 [SMILES: CCOC(=O)c1ccc(-c2cc(C)cc(C)c2)o1]

¹H NMR (300 MHz, DMSO-d₆) δ 7.46-7.42 (m, 2H), 7.38 (d, J=3.7 Hz, 1H), 7.12 (d, J=3.6 Hz, 1H), 7.06-7.03 (m, 1H), 4.32 (q, J=7.1 Hz, 2H), 2.35-2.32 (m, 6H), 1.31 (t, J=7.1 Hz, 3H)

Example 87: Preparation of ethyl 5-(3-hydroxyphenyl)furan-2-carboxylate

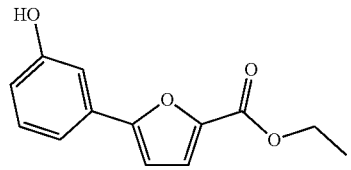 [SMILES: CCOC(=O)c1ccc(-c2cccc(O)c2)o1]

¹H NMR (300 MHz, DMSO-d₆) δ 9.71 (s, 1H), 7.38 (d, J=3.7 Hz, 1H), 7.29-7.21 (m, 3H), 7.10 (d, J=3.6 Hz, 1H), 6.83-6.79 (m, 1H), 4.31 (q, J=7.1 Hz, 2H), 1.31 (t, J=7.1 Hz, 3H)

Example 88: Preparation of ethyl 5-(quinolin-3-yl)furan-2-carboxylate

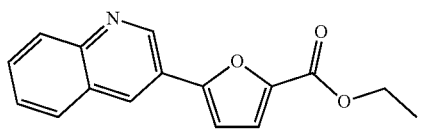 [SMILES: CCOC(=O)c1ccc(-c2cnc3ccccc3c2)o1]

¹H NMR (300 MHz, DMSO-d₆) δ 9.38 (d, J=2.3 Hz, 1H), 8.74 (d, J=2.2 Hz, 1H), 8.16-8.13 (m, 1H), 8.08-8.05 (m, 1H), 7.81 (ddd, J=8.4, 6.9, 1.5 Hz, 1H), 7.68 (ddd, J=8.1, 6.9, 1.2 Hz, 1H), 7.51-7.48 (m, 2H), 4.36 (q, J=7.1 Hz, 2H), 1.34 (t, J=7.1 Hz, 3H)

Example 89: Preparation of ethyl 5-(4-cyanophenyl)furan-2-carboxylate

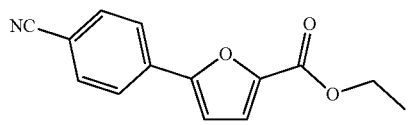 [SMILES: CCOC(=O)c1ccc(-c2ccc(C#N)cc2)o1]

¹H NMR (300 MHz, DMSO-d₆) δ 8.02-7.94 (m, 4H), 7.45 (dd, J=9.2, 3.7 Hz, 2H), 4.33 (q, J=7.1 Hz, 2H), 1.32 (t, J=7.1 Hz, 3H)

Example 90: Preparation of ethyl 5-(1H-indol-5-yl)furan-2-carboxylate

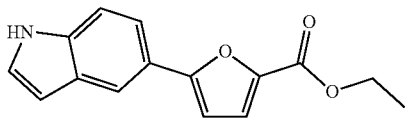 [SMILES: CCOC(=O)c1ccc(-c2ccc3[nH]ccc3c2)o1]

¹H NMR (300 MHz, DMSO-d₆) δ 11.31 (s, 1H), 8.06-8.01 (m, 1H), 7.58-7.55 (m, 1H), 7.51-7.46 (m, 1H), 7.44-7.40 (m, 1H), 7.38 (d, J=3.6 Hz, 1H), 7.02 (d, J=3.6 Hz, 1H), 6.56-6.52 (m, 1H), 4.31 (q, J=7.1 Hz, 2H), 1.32 (t, J=7.1 Hz, 3H)

Example 91: Preparation of 5-(3-hydroxyphenyl)-N-(pyridin-3-yl)furan-2-carboxamide

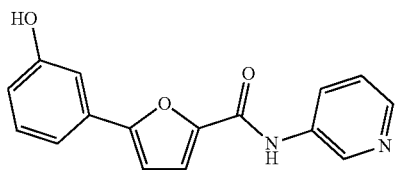 [SMILES: O=C(Nc1cccnc1)c1ccc(-c2cccc(O)c2)o1]

¹H NMR (400 MHz, DMSO) δ 10.41 (s, 1H), 9.72 (s, 1H), 8.94 (d, J=2.3 Hz, 1H), 8.34 (dd, J=4.7, 1.4 Hz, 1H), 8.19-8.16 (m, 1H), 7.48-7.35 (m, 4H), 7.29 (t, J=7.8 Hz, 1H), 7.13 (d, J=3.6 Hz, 1H), 6.84-6.81 (m, 1H)

In the following Examples 92 to 94, respective compounds were prepared in the same manner as in Example 33, except that the starting materials were changed in compliance with the structures of the respective compounds to be prepared.

Example 92: Preparation of 5-(3-(ethylcarbamoyl)phenyl)-N-isopropylfuran-2-carboxamide

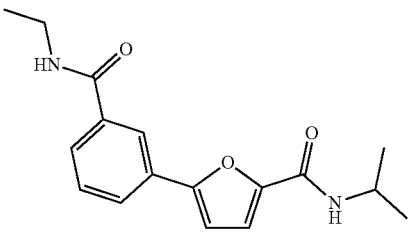 [SMILES: CCNC(=O)c1cccc(-c2ccc(C(=O)NC(C)C)o2)c1]

¹H NMR (300 MHz, DMSO) δ 8.57 (t, J=5.4 Hz, 1H), 8.27-8.23 (m, 2H), 8.07-8.05 (m, 1H), 7.81-7.78 (m, 1H), 7.56 (t, J=7.7 Hz, 1H), 7.19 (d, J=3.6 Hz, 1H), 7.13 (d, J=3.6 Hz, 1H), 4.17-4.05 (m, 1H), 3.37-3.28 (m, 2H), 1.21-1.13 (m, 9H)

Example 93: Preparation of 5-(4-(ethylcarbamoyl)phenyl)-N-isopropylfuran-2-carboxamide

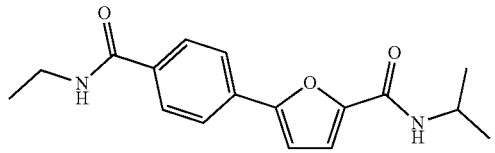 [SMILES: CCNC(=O)c1ccc(-c2ccc(C(=O)NC(C)C)o2)cc1]

$^{1}$H NMR (300 MHz, DMSO) δ 8.55 (t, J=5.4 Hz, 1H), 8.28 (d, J=8.1 Hz, 1H), 8.06-7.89 (m, 4H), 7.20 (q, J=3.6 Hz, 2H), 4.18-4.06 (m, 1H), 3.36-3.27 (m, 2H), 1.22-1.12 (m, 9H)

Example 94: Preparation of N-isopropyl-5-(4-(isopropylcarbamoyl)phenyl)furan-2-carboxamide

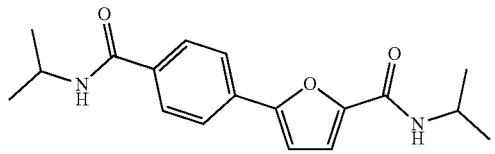 [SMILES: CC(C)NC(=O)c1ccc(-c2ccc(C(=O)NC(C)C)o2)cc1]

$^{1}$H NMR (300 MHz, DMSO) δ 8.29-8.26 (m, 2H), 8.02-7.88 (m, 4H), 7.21-7.17 (m, 2H), 4.17-4.06 (m, 2H), 1.21-1.17 (m, 12H)

Comparative Example

Compound (5-(3,4-dimethoxyphenyl)-N-isopropylthiophene-2-carboxamide) disclosed in Example 1 of Korean Patent Publication No. 10-2017-0022790 was used as a comparative example.

Experimental Example 1: Effect of Activation of Autophagy

1) Method for Autophagy Activation

The degree of autophagy activation of each compound was evaluated by measuring the degree of LC3-II production in Hep3B cells.

Specifically, Hep3B human hepatocytes were cultured in DMEM medium at 37° C. under 5% $CO_2$ atmosphere. The respective cells were dispensed into 6-well plates at a density of 5×10$^5$ cells/well. These cells were treated with DMSO, the compound prepared in Examples described above, and the compound of Comparative Example, respectively, and then treated in DMEM medium at 37° C. under 5% $CO_2$ atmosphere for 12 hours to induce autophagy. Subsequently, Hep3B cells were lysed with an extraction buffer containing protease inhibitor cocktail (PBS solution containing 0.5% Triton X-100, 1 mM $Na_3VO_4$, etc.), and then fragmentation of DNA was performed by sonication. The amount of protein was measured with bovine serum albumin as a protein standard using SMART™ BCA Protein Assay kit from iNtRON Biotechnology. After electrophoresis of 10~50 μg of total cell protein in 8~12% (w/v) polyacrylamide gel containing 0.1% SDS, the proteins present in a gel were transferred to PVDF membrane by an electroblotting technique. Then, in order to block non-specific binding, the PVDF membrane was placed in a TBS-tween (tris-buffered saline-tween, Sigma Co.) solution containing 5% non-fat dry milk and reacted at room temperature for 1 hour. The filter was placed in a TBS-tween solution containing a specific antibody against LC3 protein (Cell Signaling), allowed to stand at 4° C. for 12 hours, and then labeled with a secondary antibody labeled with HRP (Horseradish Peroxidase, Sigma Co., Cat No. P0889). Then, bands were measured using ECL (Enhanced Chemiluminescence, Thermo Scientific, Cat No. 34080).

2) Results of Measurement of Autophagy Activation

The induction of autophagy can be confirmed by an increase in specific LC3-II molecules. LC3 precursors are usually scattered in the cytoplasm, proteolytically cleaved, and present in the form of LC3-I. When autophagy is activated, the C-terminal glycine is modified to form LC3-II, which migrates to autophagosome and is distributed in puncta form.

The measurement results are shown in Table 1 below. The amount of LC3-II increased by the compound treatment was quantified by measuring the band density, and then compared with the amount of LC3-II increased by the treatment of the compound of Comparative Example, and the comparison values are shown in Table 1. That is, the case having the same autophagy-inducing capacity as that of the compound of Comparative Example is represented by a value of 1; the case having superior autophagy-inducing capacity to that of the compound of Comparative Example is represented by a value greater than 1; and the case having weaker autophagy-inducing capacity than that of the compound of Comparative Example is represented by a value less than 1.

TABLE 1

| Example No. | Autophagy-inducing capacity |
| --- | --- |
| Example 1 | 1.48 |
| Example 2 | 1.38 |
| Example 4 | 1.16 |
| Example 5 | 1.80 |
| Example 7 | 1.24 |
| Example 11 | 2.13 |
| Example 12 | 1.19 |
| Example 14 | 1.13 |
| Example 15 | 1.50 |
| Example 17 | 1.99 |
| Example 18 | 1.13 |
| Example 27 | 1.01 |
| Example 28 | 1.60 |
| Example 30 | 1.02 |
| Example 31 | 1.49 |
| Example 48 | 1.46 |
| Example 49 | 1.51 |
| Example 58 | 1.10 |
| Example 65 | 1.66 |
| Example 72 | 1.08 |
| Example 85 | 1.09 |
| Example 88 | 1.02 |
| Example 89 | 1.64 |
| Example 91 | 1.33 |
| Example 92 | 1.41 |
| Example 93 | 1.19 |
| Example 94 | 1.17 |
| Comparative Example | 1.00 |

As shown in Table 1 above, it can be confirmed by an increase in LC3-II that Hep3B cells induce autophagy by the treatment of the compound of Comparative Example used as a control substance. Also, the compound according to the present disclosure showed an increase in LC3-II as compared with the compound of Comparative Example. Therefore, it can be seen that the compounds according to the present disclosure had excellent autophagy-inducing capacity.

Experimental Example 2: Confirmation of Efficacy Against Non-Alcoholic Steatohepatitis, Liver Fibrosis and Cirrhosis In order to confirm the efficacy of the compounds of the present disclosure on nonalcoholic steatohepatitis and hepatic fibrosis, animal experiments were performed.

Specifically, to 48 mice having induced nonalcoholic steatohepatitis (8 mice for each experimental example below), between 6 and 9 weeks of age, the compound of Example 1 was divided into low-, medium-, and high-dose groups along with a vehicle (10% HPbCD in 0.5% CMC solution), and orally administered twice daily.

As a comparative group, 4 normal mice were not treated until 9 weeks of age. As a positive control, to 8 mice having induced nonalcoholic steatohepatitis, telmisartan which is a therapeutic agent of hypertension between 6 and 9 weeks of age, and obeticholic acid (OCA) currently being developed as a therapeutic agent of NASH were respectively administered orally once daily at a dose of 10 mg/kg, 30 mg/kg. As a negative control, to 8 mice having induced nonalcoholic steatohepatitis, only 10 mL/kg of a 10% HPbCD in 0.5% CMC solution which is a vehicle between 6 and 9 weeks of age was orally administered twice daily.

Subsequently, the degree of steatosis, inflammation and ballooning was measured for the liver of the 9-week-old experimental animals using HE staining, and the area of fibrosis was observed and measured using Sirius red staining. The results are scored using Bonferroni Multiple Comparison Test, and shown in FIGS. 1 and 2.

Figure 2:
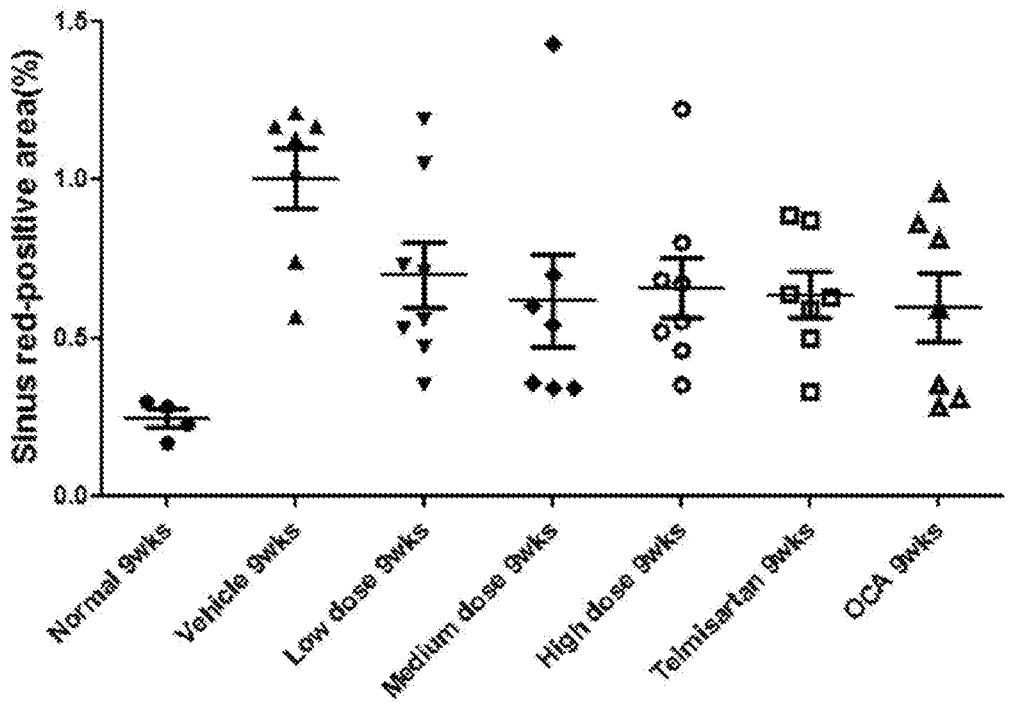
FIG. 2 is a graph that shows the area of fibrosis by staining the level of fibrosis for the liver of experimental animals.

FIG. 1 is a graph showing the nonalcoholic fatty liver disease (NAFLD) activity score calculated from a composite score of steatosis, inflammation and ballooning in the liver of experimental animals. As shown in FIG. 1, it can be confirmed that the compound of the present disclosure had significant activity for alleviation of nonalcoholic steatohepatitis in a dose-dependent manner. FIG. 2 is a graph that shows the area of fibrosis by staining the level of fibrosis for the liver of experimental animals. It was confirmed that the mice to which the compound of the present disclosure was administered exhibited a fibrosis-suppressing activity depending on the dose of the above-mentioned derivative.

The invention claimed is:
1. A compound selected from the group consisting of:
1) 5-(4-hydroxy-3-methoxyphenyl)-N-isopropylthiophene-2-carboxamide,
2) 5-(3-hydroxy-4-methoxyphenyl)-N-isopropylthiophene-2-carboxamide,
3) 5-(3,4-dihydroxyphenyl)-N-isopropylthiophene-2-carboxamide,
4) 5-(3-hydroxyphenyl)-N-isopropylthiophene-2-carboxamide,
5) 5-(4-hydroxyphenyl)-N-isopropylthiophene-2-carboxamide,
6) N-isopropyl-5-(2-methoxypyridin-3-yl)thiophene-2-carboxamide,
7) N-isopropyl-5-(6-methoxypyridin-3-yl)thiophene-2-carboxamide,
8) 5-(6-ethoxypyridin-3-yl)-N-isopropylthiophene-2-carboxamide,
9) N-isopropyl-5-(5-methoxypyridin-3-yl)thiophene-2-carboxamide,
10) 5-(1H-indol-5-yl)-N-isopropylthiophene-2-carboxamide,
11) 5-(2,6-dimethoxypyridin-3-yl)-N-isopropylthiophene-2-carboxamide,
12) 5-(6-aminopyridin-3-yl)-N-isopropylthiophene-2-carboxamide,
13) 5-(6-amino-5-methoxypyridin-3-yl)-N-isopropylthiophene-2-carboxamide,
14) N-isopropyl-5-(isoquinolin-4-yl)thiophene-2-carboxamide,
15) 5-(6-cyanopyridin-3-yl)-N-isopropylthiophene-2-carboxamide,
16) N-isopropyl-5-(quinolin-3-yl)thiophene-2-carboxamide,
17) 5-(3-aminophenyl)-N-isopropylthiophene-2-carboxamide,
18) methyl 4-(5-(isopropylcarbamoyl)thiophen-2-yl)benzoate,
19) 4-(5-(isopropylcarbamoyl)thiophen-2-yl)benzoic acid,
20) 5-(2-aminophenyl)-N-isopropylthiophene-2-carboxamide,
21) methyl 3-(5-(isopropylcarbamoyl)thiophen-2-yl)benzoate,
22) 3-(5-(isopropylcarbamoyl)thiophen-2-yl)benzoic acid,
23) N-isopropyl-5-p-tolylthiophene-2-carboxamide,
24) 5-(4-ethylphenyl)-N-isopropylthiophene-2-carboxamide,
25) N-isopropyl-5-(4-isopropylphenyl)thiophene-2-carboxamide,
26) 5-(3,4-difluorophenyl)-N-isopropylthiophene-2-carboxamide,
27) 5-(3,5-dimethylphenyl)-N-isopropylthiophene-2-carboxamide,
28) N-isopropyl-5-m-tolylthiophene-2-carboxamide,
29) 5-(2,4-dimethylphenyl)-N-isopropylthiophene-2-carboxamide,
30) 5-(4-cyanophenyl)-N-isopropylthiophene-2-carboxamide,
31) N-isopropyl-5-(4-(isopropylcarbamoyl)phenyl)thiophene-2-carboxamide,
32) 5-(3,5-difluorophenyl)-N-isopropylthiophene-2-carboxamide,
33) 5-(4-ethoxyphenyl)-N-isopropylthiophene-2-carboxamide,
34) 5-(4-(ethylcarbamoyephenyl)-N-isopropylthiophene-2-carboxamide,
35) N-isopropyl-5-(4-(phenylcarbamoyl)phenyl)thiophene-2-carboxamide,
36) 5-(2,4-dimethylphenyl)-N-isopropylfuran-2-carboxamide,
37) 5-(3,4-difluorophenyl)-N-isopropylfuran-2-carboxamide,
38) 5-(4-ethylphenyl)-N-isopropylfuran-2-carboxamide,
39) N-isopropyl-5-m-tolylfuran-2-carboxamide,
40) 5-(4-ethoxyphenyl)-N-isopropylfuran-2-carboxamide,
41) N-isopropyl-5-p-tolylfuran-2-carboxamide,
42) N-isopropyl-5-(4-isopropylphenyl)furan-2-carboxamide,
43) 5-(4-cyanophenyl)-N-isopropylfuran-2-carboxamide,
44) N-ethyl-5-(pyridin-3-yl)thiophene-2-carboxamide,
45) 5-(3,4-difluorophenyl)-N-phenylfuran-2-carboxamide,
46) 5-(4-hydroxy-3-methoxyphenyl)-N-isopropylfuran-2-carboxamide,

47) N,5-di(pyridin-3-yl)thiophene-2-carboxamide,
48) 5-(4-hydroxy-3-methoxyphenyl)-N-phenylfuran-2-carboxamide,
49) N,5-di(pyridin-3-yl)furan-2-carboxamide,
50) 5-(4-hydroxy-3-methoxyphenyl)-N-(pyridin-3-yl)furan-2-carboxamide,
51) 5-(4-hydroxy-3-methoxyphenyl)-N-(pyridin-3-yl)thiophene-2-carboxamide,
52) 5-(2-aminophenyl)-N-isopropylfuran-2-carboxamide,
53) N-isopropyl-5-(quinolin-3-yl)furan-2-carboxamide,
54) N-isopropyl-5-(2-oxoindolin-5-yl)furan-2-carboxamide,
55) 5-(1H-indol-5-yl)-N-isopropylfuran-2-carboxamide,
56) N-isopropyl-5-(isoquinolin-4-yl)furan-2-carboxamide,
57) N-isopropyl-5-(pyridin-3-yl)furan-2-carboxamide,
58) isopropyl 5-(pyridin-3-yl)furan-2-carboxylate,
59) phenyl 5-(pyridin-3-yl)furan-2-carboxylate,
60) pyridin-3-yl 5-(pyridin-3-yl)furan-2-carboxylate,
61) isopropyl 5-(pyridin-3-yl)thiophene-2-carboxylate,
62) pyridin-3-yl 5-(pyridin-3-yl)thiophene-2-carboxylate,
63) 5-(3-hydroxyphenyl)-N-isopropylfuran-2-carboxamide,
64) 5-(3,5-difluorophenyl)-N-isopropylfuran-2-carboxamide,
65) 5-(3,5-dimethylphenyl)-N-isopropylfuran-2-carboxamide,
66) 5-(3-hydroxyphenyl)-N-(pyridin-3-yl)furan-2-carboxamide,
67) 5-(3-(ethylcarbamoyl)phenyl)-N-isopropylfuran-2-carboxamide,
68) 5-(4-(ethylcarbamoyl)phenyl)-N-isopropylfuran-2-carboxamide, and
69) N-isopropyl-5-(4-(isopropylcarbamoyl)phenyl)furan-2-carboxamide.

2. A method for treating a disease associated with autophagy regulation in a subject in need thereof, comprising administering to the subject the compound of claim 1 or a pharmaceutically acceptable salt thereof,
wherein the disease associated with autophagy regulation is selected from the group consisting of liver fibrosis, liver cirrhosis, hepatitis, alcoholic liver disease, non-alcoholic fatty liver disease, non-alcoholic steatohepatitis, age-related macular degeneration, and inflammatory bowel disease.

* * * * *